United States Patent
Vacca et al.

(10) Patent No.: US 8,159,670 B2
(45) Date of Patent: Apr. 17, 2012

(54) METHOD AND APPARATUS FOR RAPIDLY COUNTING AND IDENTIFYING BIOLOGICAL PARTICLES IN A FLOW STREAM

(75) Inventors: Giacomo Vacca, Santa Clara, CA (US); Richard G. Kendall, Miami, FL (US); Norman R. Goldblatt, Los Altos, CA (US); Michael W. Yee, Mount Shasta, CA (US); Mahesh R. Junnarkar, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 579 days.

(21) Appl. No.: 12/262,431

(22) Filed: Oct. 31, 2008

(65) Prior Publication Data

US 2009/0142765 A1 Jun. 4, 2009

Related U.S. Application Data

(60) Provisional application No. 60/985,360, filed on Nov. 5, 2007.

(51) Int. Cl.
*G01N 21/00* (2006.01)
(52) U.S. Cl. .......................... 356/337; 356/338
(58) Field of Classification Search .......... 356/336–343, 356/317–318, 39, 72–73, 23–26, 441–442; 382/133; 250/461.2, 573–575, 564–565; 422/73; 436/63
See application file for complete search history.

(56) References Cited

U.S. PATENT DOCUMENTS 4,579,136 A 4/1986 Oman et al.
(Continued)

FOREIGN PATENT DOCUMENTS

DE 43 09 328 C2 9/1994
(Continued)

OTHER PUBLICATIONS

Abbott Diagnostics. CELL-DYN Sapphire™. Products [online], [retrieved on Nov. 25, 2007]. Retrieved from the Internet: <URL: http://www.abbottdiagnostics.com/Products/Instruments_by_Platform/default.cfm?system=CELL-DYN&suffix=Sapphire>, pp. 1-5.
(Continued)

*Primary Examiner* — Tri T Ton
(74) *Attorney, Agent, or Firm* — Edward J. Baba; Peter A. Socarras; Bozicevic, Field & Francis LLP

(57) ABSTRACT

A method for increasing the throughput, or the precision, or both the precision and the throughput, of a flow cytometer, or of a hematology analyzer employing a flow cytometer, and for further reducing the complexity of such a cytometer or analyzer, by utilizing the technique of laser rastering in combination with a lysis-free single-dilution method. Laser rastering involves sweeping a laser beam across a flowing sample stream in a hematology analyzer. A lysis-free single-dilution method involves performing all the flow cytometer measurements on a sample using a single aliquot, a single lysis-free reagent solution, a single dilution, and a single pass of said dilution through the measurement apparatus. An apparatus suitable for carrying out the method of this invention comprises an optical module comprising a source of light, a scanning device, a lens or system of lenses, a flowcell, detectors, and filters; and an electronic module comprising preamplifiers, analog signal conditioning elements, analog-to-digital converters, field-programmable gate arrays, digital signal processing elements, and data storage elements.

24 Claims, 24 Drawing Sheets

U.S. PATENT DOCUMENTS

| | | | |
|---|---|---|---|
| 4,920,275 A | 4/1990 | Itoh | |
| 4,999,513 A | 3/1991 | Ito et al. | |
| 5,017,497 A | 5/1991 | Gerard de Grooth et al. | |
| 5,072,382 A | 12/1991 | Kamentsky | |
| 5,083,014 A | 1/1992 | Kosaka | |
| 5,125,737 A | 6/1992 | Rodriguez et al. | |
| 5,138,181 A | 8/1992 | Lefevre et al. | |
| 5,242,792 A | 9/1993 | Rudolph et al. | |
| 5,350,695 A | 9/1994 | Colella et al. | |
| 5,426,499 A | 6/1995 | Kosaka et al. | |
| 5,444,527 A | 8/1995 | Kosaka | |
| 5,469,251 A | 11/1995 | Kosaka et al. | |
| 5,521,699 A | 5/1996 | Kosaka et al. | |
| 5,523,207 A | 6/1996 | Kamentsky et al. | |
| 5,548,395 A | 8/1996 | Kosaka | |
| 5,644,388 A | 7/1997 | Maekawa et al. | |
| 5,812,419 A | 9/1998 | Chupp et al. | |
| 5,824,269 A | 10/1998 | Kosaka et al. | |
| 5,939,326 A | 8/1999 | Chupp et al. | |
| 5,962,238 A | 10/1999 | Sizto et al. | |
| 6,002,788 A | 12/1999 | Luther | |
| 6,524,858 B1 * | 2/2003 | Zelmanovic et al. | 436/10 |
| 6,579,685 B1 | 6/2003 | Russell et al. | |
| 6,603,537 B1 | 8/2003 | Dietz et al. | |
| 6,618,143 B2 | 9/2003 | Roche et al. | |
| 6,619,050 B2 | 9/2003 | Hozumi et al. | |
| 6,671,044 B2 | 12/2003 | Ortyn et al. | |
| 6,687,395 B1 | 2/2004 | Dietz et al. | |
| 6,975,400 B2 | 12/2005 | Ortyn et al. | |
| 7,344,890 B2 | 3/2008 | Perez et al. | |
| 7,619,646 B2 * | 11/2009 | Freifeld et al. | 348/85 |
| 2002/0057432 A1 | 5/2002 | Ortyn et al. | |
| 2002/0146734 A1 | 10/2002 | Ortyn et al. | |
| 2003/0143117 A1 | 7/2003 | Nagai et al. | |
| 2005/0280817 A1 | 12/2005 | Horchner et al. | |
| 2006/0203226 A1 * | 9/2006 | Roche et al. | 356/39 |
| 2008/0158561 A1 | 7/2008 | Vacca et al. | |

FOREIGN PATENT DOCUMENTS

| | | |
|---|---|---|
| EP | 0501005 B1 | 9/1992 |
| EP | 0681178 B1 | 11/1995 |
| EP | 1 376 135 B1 | 1/2004 |
| JP | 01270644 | 10/1989 |
| JP | 02105041 | 4/1990 |
| JP | 03150444 | 6/1991 |
| WO | 9014589 A1 | 11/1990 |
| WO | 03023368 A1 | 3/2003 |
| WO | 2006004699 A1 | 1/2006 |
| WO | 2008082813 A1 | 7/2008 |

OTHER PUBLICATIONS

Innovadyne Technologies, Inc., pipetting solutions at Innovadyne Technologies, [online], [retrieved on Apr. 30, 2009]. Retrieved from the Internet: <URL: <http://www.innovadyne.com/_pipetting.html>, pp. 1-3.

Liu, et al., Bubble-induced acoustic micromixing, Lab Chip, 2002, 2, 151-157, DOI: 10.1039/b201952c, © Royal Society of Chemistry 2008.

Patterson, Dispensing Precision and Accuracy for the JANUS Varispan Automated Workstation using Versa Tip, © 2007 PerkinElmer, Inc., pp. 1-4.

University of California, Berkeley. Cancer Research Laboratory. CRL Facilities. Flow Cytometry Principles [online], [retrieved on Mar. 30, 2006]. Retrieved from the Internet: <URL: http://biology.berkeley.edu/crl/flow_cytometry_basic.html>, Mar. 30, 2006, pp. 1-6.

Vortex mixer—Wikipedia, the free encyclopedia [online], [retrieved on Apr. 30, 2009]. Retrieved from the Internet: <URL: http://en.wikipedia.org/wiki/Vortex_mixer>, pp. 1-2.

Abbott Diagnostics. Products [online]. CELL-DYN Ruby® [retrieved on Nov. 25, 2007] Retrieved from the Internet: <URL: http://www.abbottdiagnostics.com/Products/Instruments_by_Platform/default.cfm?sys_id=158>.

PCT, Notification of Transmittal of the International Search Report and the Written Opinion of the International Searching Authority, or the Declaration, Date of Mailing Feb. 20, 2009.

* cited by examiner

METHOD AND APPARATUS FOR RAPIDLY COUNTING AND IDENTIFYING BIOLOGICAL PARTICLES IN A FLOW STREAM

This application claims priority to the U.S. Provisional Application Ser. No. 60/985,360, filed Nov. 5, 2007.

BACKGROUND OF THE INVENTION

1. Field of the Invention

This invention relates to flow cytometers and hematology analyzers, and, more particularly, to hematology analyzers that count and identify biological cells using light scattering and fluorescence techniques in an optical flowcell.

2. Discussion of the Art

Flow cytometry is a technique for counting, examining, and sorting microscopic particles suspended in a stream of fluid. Flow cytometry allows simultaneous, multiparametric analysis of the physical and/or biochemical characteristics of single cells flowing through an optical/electronic detection apparatus. When used in hematology analyzers, flow cytometry enables the precise counting of cells in a measured volume of blood or other biological fluid sample and the identification of those cells based on the use of light scattering and/or fluorescence detection. As used herein, the phrase "flow cytometry" refers to the techniques and apparatus used in flow cytometers as well as in flow-cytometry-based hematology analyzers and other diagnostic instruments.

In flow cytometry, a beam of light, such as, for example, laser light of a single wavelength, light of a broader spectral nature from a light-emitting diode (LED), or some other source of light, is directed onto a hydrodynamically focused stream of a fluid carrying particles, or onto such a stream otherwise confined. A number of detectors are aimed at the region where the stream passes through the light beam, one or more detectors being in line with the light beam and typically several detectors positioned perpendicular to the light beam. The detector(s) in line with the light beam detect forward scatter, in one or more angular annuli or regions, or optical extinction, or both forward scatter and optical extinction. The detectors positioned perpendicular to the light beam detect side scatter, fluorescence, or both side scatter and fluorescence. Each suspended particle passing through the beam scatters the light in some way, and fluorescent chemicals in, or on, the particle, and either natively present in the particle or added to it during an incubation step, may be sufficiently excited to emit light at a longer wavelength than that of the light source. The combination of absorption, scattered light, and fluorescent light is detected by the detectors, and by analyzing fluctuations in intensity at each detector (typically one detector for each desired fluorescent emission band and one detector for each annulus or region of scattering angles), it is possible to determine various facts about the physical and biochemical structure of each individual particle. Forward scatter correlates with the volume of the cell and side scatter depends on the complexity of the particle, such as, for example, the shape of the nucleus, the amount and type of cytoplasmic granules or the roughness of the cellular membrane. Fluorescent markers can be conjugated with monoclonal antibodies that selectively bind to antigens present on certain types of cells or to cells in a particular pathological state; fluorescent dyes that bind selectively to nucleic acids in either the cytoplasm, cellular nucleus, or both, may also be employed. Representative examples of instruments employing flow cytometers are described in U.S. Pat. Nos. 5,017,497; 5,138,181; 5,350,695; 5,812,419; 5,939,326; 6,579,685; 6,618,143; and United States Patent Publication No. 2003/0143117 A1. These documents describe a flowing stream of cells and a stationary beam.

A subfield of cytometry, laser scanning cytometry (LSC), involves scanning a laser beam across a field of interrogation. However, the field of interrogation is stationary, typically a section of a microscope slide to which cells have been adhered, and the measurement rate (i.e., the number of cells analyzed in a given unit of time) obtainable through such a scheme is far below what can be obtained by conventional flow cytometry. Furthermore, LSC is an imaging method suitable for detailed analysis of a relatively limited number of cells, whereas flow cytometry is a light-scattering and fluorescence-tagging method of analyzing large quantities of cells. See, for example, U.S. Pat. Nos. 5,072,382, 5,523,207, and 6,002,788. Two other techniques closely related to LSC are volumetric capillary cytometry (see, for example, U.S. Pat. No. 5,962,238 and European Patent No. 0681/78) and microvolume LSC (see, for example, U.S. Pat. Nos. 6,603,537 and 6,687,395, and United States Patent Publication No. 2005/0280817). All of these techniques rely on a scanning laser beam impinging upon a specimen fixed to a controllable stage and on methods based on highly resolved imaging, confocal scanning, or spectroscopy techniques.

Several teachings in the prior art describe an imaging flow cytometer that combines the flow characteristics of a conventional analyzer with imaging capabilities. See, for example, U.S. Pat. Nos. 5,083,014, 5,444,527, 5,521,699, 5,644,388, 5,824,269, 6,671,044, and 6,975,400, and United States Patent Publication Nos. 2002/0146734 and 2002/0057432. In the prior art, (a) the laser or other light source is stationary, necessitating the use of a charge-coupled detector (CCD) array in order to capture information from across the field of interrogation; and (b) the information obtained is of an imaging nature rather than of a scattering nature. This approach causes the process to run significantly more slowly than in flow cytometry; in other words, in order to obtain more detailed information for each cell by the use of the disclosed imaging strategy, the measurement rate is reduced, i.e., the overall number of cells actually analyzed in a given unit of time is reduced.

One of the key advantages of imaging methods is that such methods are capable of capturing fine details of individual cells, which enable a trained professional to make positive identifications in borderline cases. However, the greater detail obtainable by imaging methods are balanced by the reduction in the total number of cells that can be analyzed in this way in a given period of time. In methods based on scattering, identification is based on characteristics that are averaged over the cell (such as cell size, hemoglobin content, lobularity of the nucleus, etc.); however, the loss of fine detail in individual cells is compensated for by the ability to collect desired information for tens of thousands of cells in a matter of seconds. Such information can be used to plot the results in aggregate according to a few characteristics (such as, for example, size, lobularity, etc.).

The CELL-DYN® Sapphire® hematology analyzer (commercially available from Abbott Laboratories), an instrument based in part on flow cytometry, processes a minimum of 105 complete blood count (CBC) samples per hour under standard conditions. This aspect of performance is referred to as the throughput of the instrument. Other commercially available hematology analyzers are capable of processing up to 150 standard CBC samples per hour, although the performance tradeoffs adopted in their designs usually result in higher rates of reflex testing, slide review, or both reflex testing and slide review. It would be desirable to increase the effective throughput of hematology analyzers (i.e., accounting for both the mechanical throughput and the rate of first-pass reportability) so as to be able to process a higher volume of standard CBC samples per hour than currently possible, while at the same time maintaining a low rate of reflex testing and slide review. This improvement would enable use of such an analyzer in a high-volume laboratory (reference laboratory or hospital core laboratory), which requires the processing of large numbers of standard, mainly normal, CBC samples per day with as few slide reviews as possible. It would also enable higher throughput of samples in any of the other laboratory environments where an analyzer is used.

There are several obstacles to higher throughput, such as, for example, loading samples, aspirating samples, dispensing samples, diluting samples, mixing samples, incubating samples, staging samples, delivering samples to the flowcell, and the time required for a sequential measurement of a series of samples. These obstacles can be thought of as bottlenecks, where the narrowest bottleneck determines the overall throughput of the instrument. The current narrowest bottleneck in the CELL-DYN®Sapphire® instrument is the time involved in the sequential measurements through the optical flowcell. The performance currently achieved involves a compromise between acceptable levels of coincidences, acceptable precision of results (total number of cells counted), constraints from the present hardware/electronics architecture, i.e., arrangement of hardware and electronic components, and constraints from the assay strategy involving reagents and dilution. As used herein, a "coincidence" is interpreted to mean an event where two or more cells, either of a similar type or a dissimilar type, are sufficiently close that they cannot be resolved by the instrument, are counted as one, and are misidentified in one or more detection parameters.

Increasing the flow rate through the flowcell by widening the sample stream, by increasing the velocity of the sample stream, or both of the foregoing, have all been attempted. In a conventional flow cytometer, where the sample stream is intersected by a stationary beam, the measurement rate in the linear regime (defined as the number of cells being analyzed per second, n) is given by $$n = \rho x_{stream} z_{stream} v_{steam}, \quad \text{(Eq. 1)}$$

where $\rho$ represents the concentration of cells in the sample stream, $x_{stream}$ represents the transverse dimension of the illuminated portion of the sample stream, $z_{stream}$ represents the longitudinal dimension of the illuminated portion of the sample stream, and $v_{stream}$ represents the flow velocity. In order to increase the measurement rate, one can attempt to increase any one of those four quantities. However, under the circumstances encountered in the state of the art, increasing $\rho$ leads to greater coincidence events, as does increasing $x_{stream}$ and $z_{stream}$. Increasing $v_{stream}$ can lead to risks related to the onset of turbulence or other kind of hydrodynamic instability, which can severely reduce the precision of the measurements, because the resulting sample stream oscillates or fluctuates unpredictably across a stationary light beam.

Other options include simply doubling the entire measurement hardware, with two sets of measurements occurring in parallel on separate flowcells interrogated by separate sources of light. Two sources of light can be employed or a single source of light can be split into two. The shortcomings of this approach are increased complexity, a greatly increased cost, a greatly increased risk to reliability because of the large number of additional components, and increased service costs.

U.S. patent application Ser. No. 11/934,277, incorporated in full herein by reference, addresses satisfactorily the issues described above, namely improving the throughput of a flow cytometer without incurring higher coincidences, without degrading precision of results, without greatly changing the hardware and/or electronics (and consequently having to meet most of the same constraints), without necessarily changing the chemistries and dilutions currently in use, and while maintaining the currently available desirable attributes associated with a high rate of first-pass reportability of results. That disclosure describes a method and apparatus capable of achieving a significant improvement in performance with relatively limited changes in the architecture and operation of a current analyzer. While such limited scope of design changes is attractive and beneficial from a commercial viewpoint, it also constrains the degree to which the innovations described in the concurrent disclosure can be exploited.

In hematological assays aimed at determining parameters from human whole blood, there are two physiological factors that present obstacles to simple, rapid, and accurate determination of cell counts. One factor is that, in typical fresh peripheral human whole blood, there are about 1,000 red blood cells (RBCs) and about 50 platelets for each white blood cell (WBC). The other factor is that, while platelets are typically sufficiently smaller than any other cell type to allow discrimination based on size, and most white blood cells (WBCs) are sufficiently larger than either RBCs or platelets to again allow discrimination based on size, two cell species in particular—RBCs and lymphocytes, a subtype of WBCs—typically overlap in size distribution (as well as in their scattering signatures) to a sufficient degree to make discrimination based on size prone to gross error. Therefore, when determining RBCs mainly by size discrimination, the asymmetry in concentration works in one's favor, since the occasional WBC misclassified as a RBC will not, generally, affect the overall accuracy of the measured concentration of RBCs to any appreciable degree; however, the converse is not true, and any unaccounted for interference from RBCs in determining the concentration of lymphocytes (and, by extension, the overall concentration of WBCs) would yield very inaccurate results.

Consequently, methods have been developed in the prior art to handle this large asymmetry and size overlap and still provide useful results in an acceptable time frame. One standard method employed in the prior art has been to separate the blood sample to be analyzed into at least two aliquots, one destined for RBC and platetet analysis, and one for WBC analysis. The aliquot destined for WBC analysis is mixed with a reagent solution containing a lysing reagent that preferentially attacks the membranes of the RBCs. Partially on account of their loss of hemoglobin through the compromised membrane, and partially on account of their attendant reduction in size, the resulting lysed RBCs become distinguishable from lymphocytes based on their respective scattering signatures. Another method employed in the prior art involves using nucleic acid dyes to provide a fluorescent distinction between the RBCs and the WBCs. WBCs contain a nucleus containing DNA. When these WBCs are labeled via a fluorescent label, they can be distinguished from mature RBCs, whose nuclei have been expelled in the maturation process.

Both of these methods have drawbacks. First of all, the lysing reagent used to dissolve the RBCs can attack the WBCs as well, reducing their integrity and eventually dissolving them, too. This is particularly a problem with WBCs that are already fragile in the first place, due to some pathological condition (such, as, for example, chronic lymphocytic leukemia). At the other end are types of RBCs (such as, for example, those found in neonates, and in patients with thalassemia, sickle-cell anemia, and liver disease) which are naturally resistant to lysis, and which therefore tend to persist as interferents in WBC assays involving lysis. In order to reduce the likelihood of either degradation of WBCs or interference from unlysed RBCs (either of which would jeopardize the accuracy of the overall WBC concentration measurement), a careful combination of concentration of lysing agent, temperature control, and incubation time must be used. In some cases, the user is offered several test options with different lysing conditions, thereby allowing the user to tailor the assay to the subject patient sample. This tailoring, however, is a complex solution, which additionally either requires prior knowledge of the state of the patient, or must be used as a reflex test following a standard CBC.

Regarding the fluorescence-based approach at discriminating between RBCs and lymphocytes, the main obstacle is the measurement rate. When WBCs are measured at the same time as RBCs and platelets, the presence of RBCs sets an upper limit to the concentration that can be sent through the analyzer without incurring in coincidences at an unacceptably high rate; the dilution ratio used to achieve such concentration, in turn, limits the rate at which WBCs events are being counted; and in order to obtain the counting precision expected of the analyzer, this relatively low rate of WBC event acquisition, in turn, forces long acquisition times. For example, the concept of measuring all of the components of blood from a single sample in one pass was disclosed in U.S. Pat. No. 6,524,858. As noted in that disclosure, the method would be capable of a cycle time of 88 seconds, or about 41 CBC/hr. This throughput is far lower than that achievable by most automated hematology analyzers commercially available today, severely limiting its commercial usefulness. The CELL-DYN® Sapphire®, as another example, presently offers a test selection (requiring yet another aliquot of sample in addition to those used in the RBC/platelet assay and in the WBC assay) employing a nucleic-acid dye capable of differentiating between RBCs and lymphocytes. This test selection uses the dye primarily to differentiate between mature RBCs and reticulocytes, a subset of immature RBCs that retain dye-absorbing RNA in the cytoplasm. While it would technically be possible to count the WBCs using this same assay, as they are sufficiently differentiated by fluorescence from either RBCs or reticulocytes to obtain the desired accuracy, the relatively low concentration of WBCs in the dilution used makes it an impractical option to achieve the required statistical precision. Such a scheme would require an acquisition time of approximately 75 seconds, limiting throughput to only 48 CBC/hr. Accordingly, although this approach is theoretically feasible, a much higher throughput would be required in order for this approach to become practical commercially.

A single-dilution approach presents many attractive benefits. One of them is the elimination of multiple aliquots: This feature drastically simplifies the fluidic architecture of the system, since it requires a single container (instead of two or more) in which to mix the blood sample and the reagent solution, and a single system (such as, for example, a precision metering syringe and associated driver motor and control electronics) for measuring and delivering the reagent solution to the mixing container. It also affords an attendant reduction in the number of valves, the number of valve actuators, the number of individual segments of tubing, and the number and quantity of reagents necessary to implement the desired assay. Another benefit is the elimination of the process of lysing RBCs: This feature reduces drastically the uncertainties associated with lysis-resistant RBCs and with lysis-prone lymphocytes; it eliminates the need for the time-consuming and sensitive lysis incubation period; and, additionally, it eliminates a significant portion of the software dedicated to operate the analyzer, as previously separate test selections are combined in a single procedure. Another benefit accrues from the overall reduction in complexity of the analyzer due to the individual changes just described.

There are additional potential attendant reductions in complexity. Hematology analyzers designed for high throughput also generally include additional transducers in addition to the flow cytometer subassembly incorporated therein, such as, for example, one or more impedance transducers to count, size, and identify some subpopulations of blood cells, and a colorimetric transducer to determine the hemoglobin-related parameters of blood. A single-dilution analyzer could eliminate the need for additional impedance transducers, for a colorimetric transducer for measurement of hemoglobin, or for both impedance transducers and colorimetric transducers for measurement hemoglobin, if the analyzer were capable of achieving sufficient speed in measurement to render these deletions practical. Because the colorimetric transducer for measurement of hemoglobin requires the use of a strong lysing agent to dissolve the membranes of the RBCs (the lysing agent typically being in addition to the milder lysing agent used in the WBC assays), elimination of the calorimetric transducer for measurement of hemoglobin would also eliminate the need for an additional on-board lysing agent in addition in addition to that used in the flow cytometer subassembly. The reduction in complexity, whether from simply replacing the flow cytometer subassembly of the prior art with a single-dilution subassembly while maintaining a separate colorimetric transducer for measurement of hemoglobin or an impedance transducer or both, or from additionally incorporating all the functions of impedance transducers and colorimetric transducers for measurement of hemoglobin into the single-dilution analyzer, would result in a substantial improvement in the reliability of the instrument, because the number of parts subject to failure would be reduced, and because the number of components generating potentially damaging heat would be reduced. This improvement in reliability would likewise provide a major improvement in the instrument's service profile, with less maintenance required, fewer service calls required, and a lower cost for those calls that do occur, on account of the increased serviceability of a simplified instrument architecture, i.e., an instrument having fewer components.

All of these benefits, however, are overshadowed in the prior art by the low throughput of the disclosed method. In other words, the single-dilution feature disclosed in prior art is only one of the enabling elements of a superior analyzer. It would be desirable to enhance the single-dilution approach with a high measurement rate in order to also provide the throughput performance commonly expected of commercial hematology analyzers, and typically expected of analyzers designed for high-volume environments.

SUMMARY OF THE INVENTION

This invention provides a method for increasing the measurement rate, and reducing the complexity, of a hematology analyzer based on flow cytometry, by utilizing the technique of laser rastering in combination with a method of analyzing blood or other biological fluid using a lysis-free single-dilution approach. Laser rastering involves sweeping a laser beam across a flowing sample stream in a hematology analyzer.

In a conventional flow cytometer, the stationary laser beam, generally significantly widened in the horizontal direction, intersects the comparatively narrow flowing sample stream, interacting with the cells or other particles therein and resulting in scattering, extinction, or fluorescent signals that can be detected. According to the method described in co-pending U.S. patent application Ser. No. 11/934,277, incorporated in full herein by reference, the sample stream is given a width greater than that of a sample stream in a conventional hematology analyzer, thereby increasing the flow rate of cells through the flowcell. Referring to Eq. 1, this widening operation, in effect, increases the transverse dimension Xstream of the sample stream, thereby increasing n by a proportional amount. However, this widening operation also increases the likelihood of potential coincidences.

In order to limit coincidences to acceptable levels, the spot of focused light from the light beam is reduced in the horizontal dimension so as to intercept only a portion of the resulting sample stream. Because the coincidences are governed by the magnitude of the volume of the sample stream illuminated at any one time by the laser beam, reducing the width of the laser beam to intersect only a portion of the transverse horizontal extent of the sample stream also reduces the magnitude of the illuminated volume. Such reduction is gauged to recover the size of the illuminated volume in the original, conventional design, where the coincidence rates are known and acceptable.

With a stationary laser beam, such a configuration would however "miss" a sizable portion of the sample stream, because the laser beam would now be narrower than the sample stream. In order to count all the cells (or particles) in the sample stream as they flow past the position of the focused laser beam, the laser is "rastered," or swept from side to side.

In conventional raster schemes, a spot is first moved across a given row in a given direction, then the spot is moved downwardly to the next row, the spot is then moved in a direction opposite to that traversed for the first row, the spot is again moved downwardly to the next row, and the procedure is repeated for the remaining rows in the area of interest. Alternatively, after moving across any given row, the spot is then moved downwardly by one row as well as back across so as to start the next row on the same side as the previous one. An example of a conventional raster scheme is the formation of an image on a standard cathode-ray tube television screen or computer monitor. In the method described herein, rastering results from a combination of the transverse motion of the laser beam and the vertical translation of the flowing sample stream. In other words, the laser beam only needs to be swept in the horizontal direction, because the flowing sample stream provides the vertical translation of the interrogation volume necessary for rastering. The rastering is carried out at a sufficiently high speed to allow the laser beam to interact with all the cells or particles in the sample stream, with the result that the measurement rate is increased in direct ratio to the increase in the overall quantity PXstream $z_{stream}$ Vstream in Eq. 1. It will be readily recognized by those skilled in the art that the overall coincidence level can be kept constant by, for example, decreasing $z_{stream}$ and increasing ρ proportionately. In other words, it is not necessary to constrain the level of dilution of the sample to a predetermined value, because the geometry of the core stream can be adjusted to accommodate different levels of dilution and still result in the desired increase in throughput without sacrificing coincidence performance.

To account for the varying scattered intensities derived from the interaction of the cells with different portions of the nonuniform profile of the laser beam, the raster speed and flow speed can be adjusted so as to interrogate every cell a plurality of times and obtain from this set of measurements a representative value of the peak scattered intensity.

In one embodiment, the apparatus and method of this invention employ, in addition to a laser, (a) a dynamic beam deflector (e.g., an acousto-optic deflector, hereinafter alternatively referred to as "AOD"; or an acousto-optic modulator, hereinafter alternatively referred to as "AOM") as the preferred type of component for effecting the sweeping of the light beam; (b) for each detector channel, an electronic module that includes one of each of the following components: a fast analog-to-digital converter (ADC) channel, a field-programmable gate array (FPGA) or portion thereof, and optionally a digital signal processing (DSP) chip or portion thereof; and (c) sufficient onboard memory registers to hold intermediate values for computation and storage. Additional electronic components, of both analog and digital variety, can be employed in order to provide the necessary signal conditioning steps in conjunction with the digitization and digital signal processing steps carried out by the elements in (b) and (c) above. These can include, but are not limited to, preamplifier circuitry with sufficient bandwidth, noise filtering circuitry, baseline restoration circuitry, and circuitry for compensation of light intensity variations on account of the operation of the AOD; each of these may interact with the FPGA (and optionally with the DSP) and other circuitries in order to properly carry out its intended function. The foregoing elements are substantially additions to, or replacement for, elements conventionally used in current hematology analyzers. In addition to the foregoing elements, the apparatus and method of this invention employ elements representing a reduction in the number of corresponding elements conventionally used in current hematology analyzers and flow cytometers. These elements are: (d) a reagent solution, free of a lysing agent, that includes a RNA- and DNA-staining fluorescent dye, or separate dyes that selectively bind to RNA and DNA; (e) a sample aspiration assembly capable of delivering a portion of a sample; (f) a single container for holding such portion and for mixing of such portion with the reagent solution; (g) a single subsystem for metering and delivery of the appropriate amount of reagent solution into the sample aliquot container; (h) a single subsystem for staging the resulting solution of sample aliquot and reagent to the optical flowcell; (i) fluidic components necessary for rinsing the sample path and for waste disposal.

In one embodiment of the method described herein, the analyzer maintains, besides the components previously mentioned as necessary for the operation of the rastering flowcell, a colorimetric transducer for the detection and quantification of hemoglobin, together with a lysing agent, appropriate fluidics, and appropriate electronics necessary to support the hemoglobin assay performed on such a transducer. In another embodiment of the method described herein, the analyzer does not possess a separate calorimetric transducer for the measurement of hemoglobin (and the supporting lysing agent, supporting fluidics, and supporting electronics), having incorporated the hemoglobin-quantification function of such a transducer into the function of the rastering flowcell that measures the results of a single-dilution assay free of lysing agent.

BRIEF DESCRIPTION OF THE DRAWINGS

FIG. 6A shows the laser beam during the initial phase of contact with the cell. FIG. 6B shows the laser beam significantly overlapping the cell. FIG. 6C shows the laser beam centered on the cell, with the resulting interaction being at a maximum value. FIG. 6D shows the laser beam significantly, but not maximally, overlapping the cell. FIG. 6E shows the laser beam making one of its final contacts with the cell.

FIG. 7A shows the result of an interaction wherein the laser beam first contacts a cell. FIG. 7B shows the result of an interaction wherein the same cell as in FIG. 7A has advanced further in the sample stream and interacts relatively close to the central portion of the laser beam. FIG. 7C shows the result of a third interaction wherein the same cell as in FIGS. 7A and 7B has advanced further in the sample stream and interacts with the edge of the laser beam. FIG. 7D indicates the highest values arranged by scan number (or time) on the graph, a curve (e.g., a Gaussian curve) that is mathematically extracted from these values, and the peak value of that curve.

FIG. 10 shows parameters of dimensions and dilutions utilized to explain the condition of coincidences.

FIG. 11 illustrates how the average number of particles in the illumination volume (and therefore the coincidence rates) can be maintained substantially constant, while one or more parameters of dimensions and dilutions are varied with respect to the prior art.

FIGS. 12, 12B, and 12C show the parameters of dimensions utilized to explain the requirement that each interaction provide a plurality of digitized measurements.

FIG. 13 shows the parameters of dimensions utilized to explain the requirement that the laser beam sweep across the cell a plurality of times as the cell advances in the sample stream.

FIG. 14 shows the parameters of dimensions, dilutions, and flow utilized to calculate the overall measurement rate of the system (i.e., the number of cells measured in a given unit of time).

FIG. 15 illustrates how the number of cells measured in a given unit of time can be increased while one or more of the parameters of dimensions, dilutions, and flow are varied with respect to the prior art.

FIG. 17 illustrates the reduction in subsystems and the reduction in overall complexity attendant with the introduction of laser rastering as an enabling approach in a lysis-free single-dilution analyzer that does not require a lysing agent.

DETAILED DESCRIPTION

Figure 1:
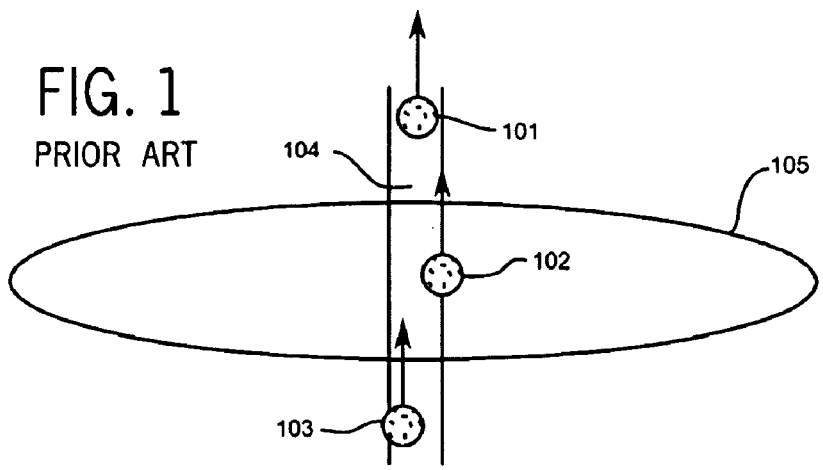
FIG. 1 is a schematic diagram illustrating the prior art from the point of view of the laser beam. The focused beam spot is elliptical with a relatively short vertical axis and a relatively long horizontal axis. The laser beam intersects the narrow sample stream so as to interrogate substantially only one cell at a time.

As used herein, the expression "laser rastering" refers to the novel method and apparatus described herein. However, it should be noted that the term "laser" is intended to include any source of light suitable for use in this invention. Such sources of light include, but are not limited to, lasers, light-emitting diodes (LEDs), arc lamps, plasmas, and any other source of light that is capable of providing sufficient brightness, stability or reproducibility or both stability and reproducibility of intensity and wavelength, and spectral purity. Likewise, in the description that follows, a laser will be referred to as an example of a suitable source of light, without implying that other sources of light are not included in the description of this invention. As used herein, the term "deflect" means to move a beam of light across a sample stream in a flowcell. Alternate expressions used herein which are intended to have substantially the same meaning as "deflect" include "scan" and "sweep." The term "rastering" means repeatedly sweeping a beam from a source of light from side to side. The expression "imaging method" refers to a method that is different from a scattering method. The expression "sample stream" means a body of running fluid, in a flowcell, in which particles from a biological sample are carried. The sample stream (e.g., a body fluid such as, for example, blood, optionally mixed with a saline solution or with a reagent solution) is typically surrounded by a sheath of fluid (e.g., phosphate buffered saline) that flows alongside of it within the flowcell, and which both provides isolation from the flowcell walls and confines the sample stream to a smaller portion of the flowcell. As used herein, the term "particle" is intended to include a biological cell and any other biological or non-biological substance having a size ranging from about 0.5 µm to about 50 µm in major dimension, e.g., diameter. In the description that follows, a cell will be referred as just one example of a suitable item presented to the apparatus for analysis; other items, such as, for example, cell fragments, nuclei, other biological particles (e.g., bacteria), or non-biological particles (e.g., beads of silica, latex, or other material, either pure or augmented, by coating, inclusion, mixing, or other method, with fluorescent substances; and either untreated or treated with conjugated monoclonal antibodies or other biological markers for use in rapid screening and other similar assays), are also included in the scope of the term "particle". As used herein, the term "lysis-free single-dilution method" refers to a method of performing analysis of blood or other biological fluids on hematology analyzers that relies on diluting a single portion of the sample in an appropriate reagent solution, processing the resulting mixture through the measurement apparatus, and thereby obtaining a number of values of parameters pertaining to such sample that would otherwise require a plurality of portions, a plurality of dilutions, and a plurality of reagent solutions, including at least one reagent solution comprising a lysing agent for cells.

As used herein, the expression "body fluid" includes, but is not limited to, such biological fluids as, for example, blood, cerebrospinal fluid, ascites fluid, pleural fluid, peritoneal fluid, pericardial fluid, synovial fluid, dialysate fluid, and drainage fluid.

Figure 4:
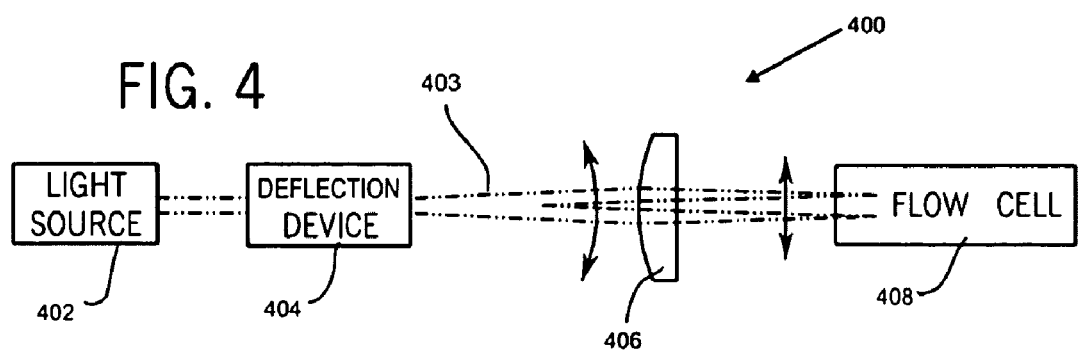
FIG. 4 is a schematic diagram illustrating the essential components of a rastering flow cytometer according to the present invention.
Figure 9:
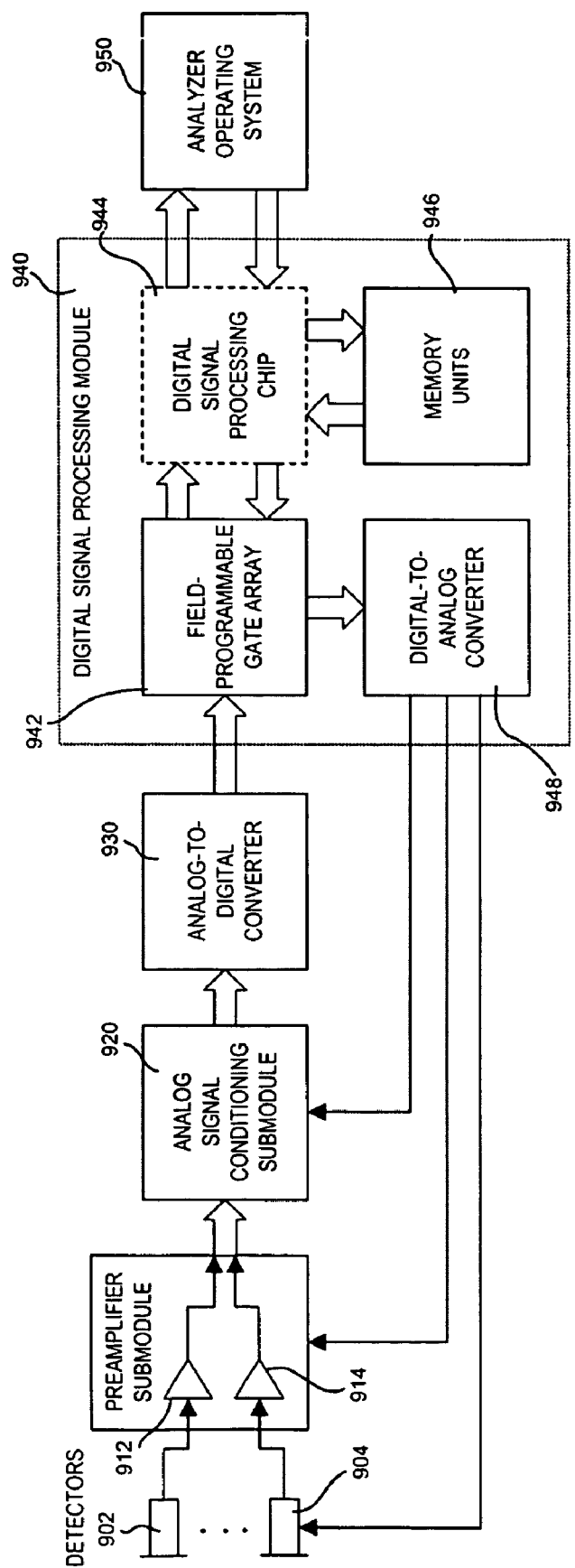
FIG. 9 is a schematic block diagram of the essential elements of the electronic module used for signal processing in the present invention.
Figure 17:
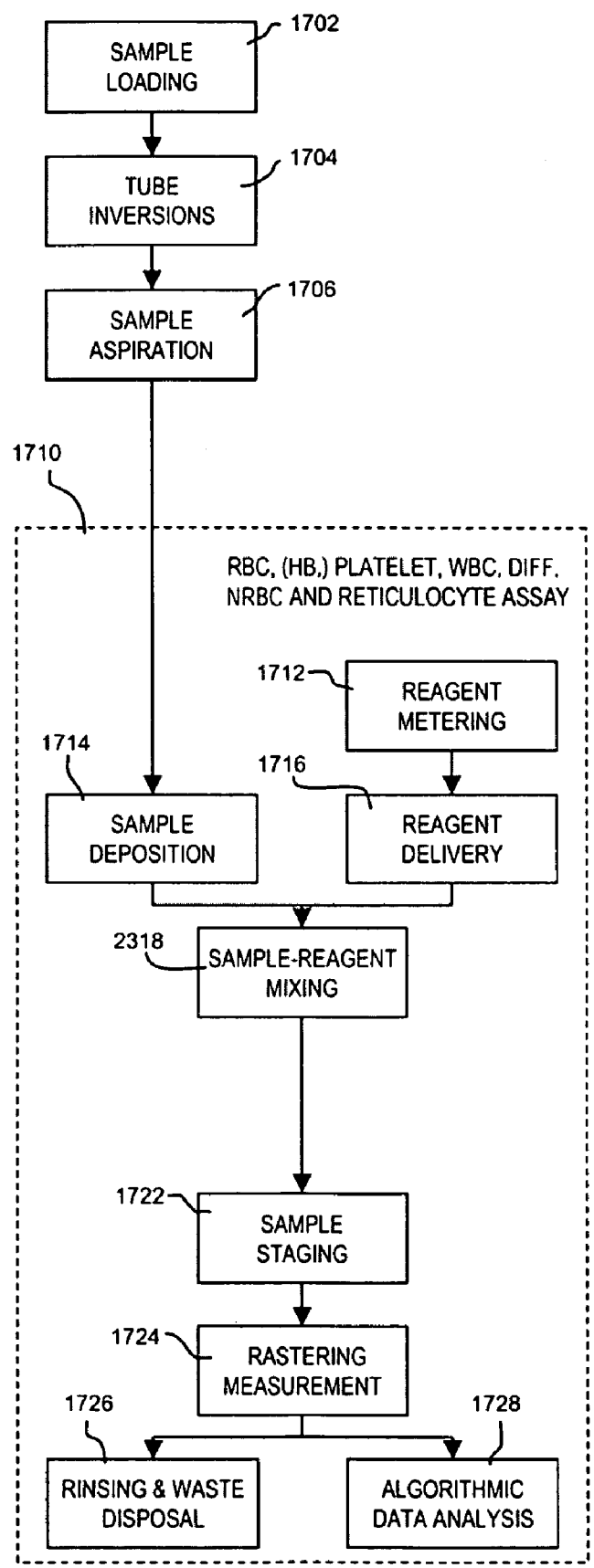
FIG. 17 is the analogue of FIG. 16 for the present invention.

The system comprises three key modules: (1) a fluidic module to prepare a solution of the sample; (2) an optical module to effect the angular sweep of a beam of light across a stream of the sample, and (3) an electronic module to process the signals derived from the optical module. The fluidic module is schematically shown in FIG. 17. The optical module described herein, with the exception of detectors, filters, and other peripheral optical components, is shown in FIG. 4. The configuration of the apparatus described herein is contrasted with the configuration of the apparatus of the prior art. The optical module of the present invention includes a deflection device, e.g., acousto-optic deflector (AOD), inserted into the optical path. The electronic module described herein is shown in FIG. 9, and it includes fast analog-to-digital converter(s) (ADC), field-programmable gate array(s) (FPGA), and optionally digital signal processing (DSP) chip(s).

The fluidic module shown in FIG. 17 represents a simplified fluidic module of the type that is well-known to one of ordinary skill in the art. The AOD is an addition to commercially available hematology analyzers currently in use. The components in the electronic module are in part substitutions for electronic components currently in use and in part additions to electronic components currently in use.

Referring now to FIG. 1, the method of obtaining data from flow cytometry equipment typically used in the prior art involves illuminating cells 101, 102, 103 moving with the sample stream 104 by means of a stationary beam of light 105, e.g., a laser beam. In FIG. 1, it can be seen that the spot (focus) of the beam of light 105, e.g., a laser beam, is elliptical in shape, with a relatively short vertical axis (y) and a relatively long horizontal axis (x); additionally, such a spot typically has an intensity profile (along either the short or the long axis) approximately described by a Gaussian curve.

Figure 2:
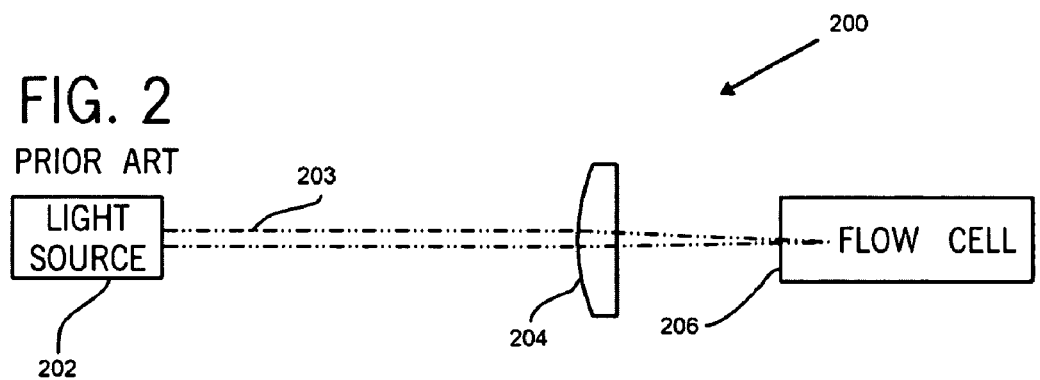
FIG. 2 is a schematic diagram illustrating the essential components of a conventional flow cytometer of the prior art.

The method shown diagrammatically in FIG. 1 can be carried out by the optical module depicted in FIG. 2. The optical module 200 shown in FIG. 2 comprises a source of light 202, a light beam 203, a lens or system of lenses 204, a flowcell 206, and detectors (not shown). For the sake of simplification, detectors, which are required, are not shown, but are well-known to those of ordinary skill in the art. Other peripheral or optional components, such as mirrors, slits, prisms, and filters, are also not shown. The electronic module is also not shown.

In the prior art, as depicted in FIG. 1, each cell 101, 102, 103 is presented a varying light beam profile in the direction of flow (vertical dimension) and a substantially uniform light beam profile over the width (horizontal dimension) of the sample stream 104 (because the beam of light 105 in the horizontal direction is made very much wider than the sample stream 104); in the prior art, the peak of the signal from the interaction between the light and the cell is found along the vertical dimension, i.e., the direction of flow.

Figure 3:
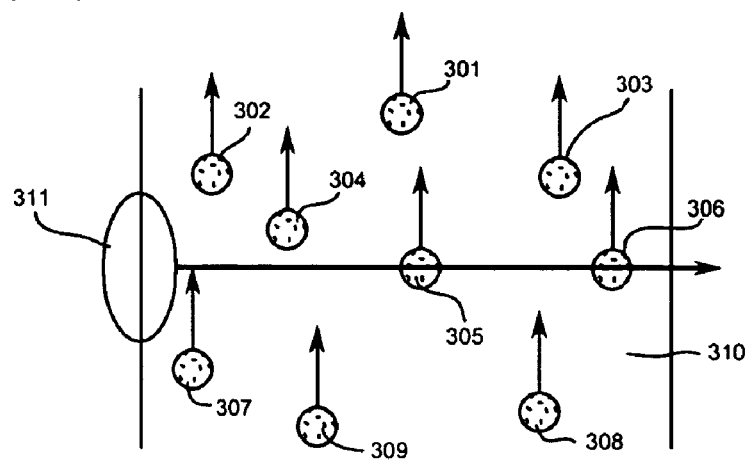
FIG. 3 is a schematic diagram illustrating a sample stream that allows more cells to flow through the volume under analysis in a given unit of time. The horizontal axis of the laser beam is greatly reduced in length, as compared with the prior art, in order to interrogate, typically, only one cell at a time. The laser beam sweeps across the significantly widened sample stream in order to intersect each cell as it flows within the sample stream.

Referring now to FIG. 3, the method of this invention involves illuminating cells 301, 302, 303, 304, 305, 306, 307, 308, 309 moving with the sample stream 310 by means of a beam of light 311, e.g., a laser beam, which is caused to raster by means of a deflection device. It can be seen that the spot (focus) of the beam of light, e.g., the laser beam, is elliptical in shape, with the vertical axis (y') being substantially equal in length to the vertical axis (y) of the beam of the prior art and the horizontal axis (x') being substantially shorter than the horizontal axis (x) of the beam of the prior art. In FIG. 3, the spot (focus) of the laser beam is caused to sweep across the flow stream in a direction parallel to the horizontal axis (x').

The method shown diagrammatically in FIG. 3 can be carried out by the optical module shown schematically in FIG. 4. In FIG. 4, the essential components of the optical module 400 are a source of light 402 for providing a beam of light 403, a deflection device 404, at least one optical element such as, for example, a lens or system of lenses 406 for focusing the beam of light 403, a flowcell 408, and at least one detector (not shown). For the sake of simplification, detectors, at least one of which is required, are not shown, but are well-known to those of ordinary skill in the art. Other peripheral or optional components, such as mirrors, slits, prisms, and filters, are also not shown. The electronic module is also not shown. The lens 406 serves the dual function of: (1) focusing the approximately collimated beam of light 403 onto the flowcell 408; and (2) converting the angular sweep of the beam of light 403 introduced by the deflection device 404 into a parallel lateral translation of the beam 403 across some portion of the flowcell 408. These functions are achieved by placing the lens 406 approximately one focal length away from the deflection device 404 and one focal length away from the flowcell 408. Other optical configurations for achieving substantially the same effect of varying the transversal position of the beam spot at the flowcell while varying as little as possible the position of the propagating beam (and any scattered beam of light or any beam of emitted fluorescent light) beyond the flowcell exist, by means of both altered locations of components, or by means of the insertion of additional components, or by means of both altered locations of components and insertions of additional components.

In the scheme of the invention described herein and depicted in FIG. 3, each cell 301, 302, 303, 304, 305, 306, 307, 308, 309 is presented a varying profile in both the horizontal direction and in the vertical direction of the sample stream 310, because the beam of light 311 is made smaller than the width of the sample stream 310. The determination of peak intensity is then achieved in two steps. In the first step, peak intensity is determined "horizontally" (across) the sample stream 310, with rapid digitization and isolation of peaks from individual raster scans in the horizontal direction. In the second step, peak intensity is determined "vertically" in the sample stream 310 by analyzing multiple raster scans and fitting the sequence of peak values to a curve that represents the profile of the beam of light 311 in the vertical direction, and extracting the peak of such a fitted curve; alternatively, such a curve and its peak can be obtained by applying appropriate digital filtering to the sequence of peak values.

The deflection device 404 can be an AOD or an AOM. The essential components of systems of the prior art include a source of light, a lens or system of lenses, a flowcell, and appropriate detectors. In both the prior art and in the method described herein, the sources of light, the lens and the systems of lenses, the flowcells, and the detectors, and the functions thereof in a flow cytometry system, are well-known to those of ordinary skill in the art. See, for example, U.S. Pat. Nos. 5,017,497; 5,138,181; 5,350,695; 5,812,419; 5,939,326; 6,579,685; 6,618,143; and United States Patent Publication No. 2003/0143117 A1, where sources of light, lenses, flowcells, and detectors are described in greater detail. All of these references are incorporated herein by reference. See also http://biology.berkeley.edu/crl/flow_cytometry_basic.html, Mar. 30, 2006, pages 1-7, incorporated herein by reference. Lasers, lenses, flowcells, and detectors suitable for use in this invention are used in commercially available instruments from Abbott Laboratories, Abbott Park, Ill., under the trademark CELL-DYN®.

Acousto-optic modulators (AOMs) and acousto-optic deflectors (AODs) are well-known in the art of laser physics and optical technology. An AOD, also sometimes known as a Bragg cell, uses the acousto-optic effect to dynamically diffract, and thereby to deflect, a beam of light using sound waves (usually at radio frequency). An AOM can also be used to shift the frequency of the light beam. AOMs are used in lasers for Q-switching, in telecommunications for signal modulation, and in spectroscopy. A piezoelectric transducer is attached to a material such as glass or quartz. An oscillating electrical signal drives the transducer to vibrate, which creates sound waves in the glass or quartz. These can be thought of as moving periodic planes of expansion and compression that change the index of refraction of the optical medium. Incoming light interacts with the resulting periodic index modulation in a process called Bragg diffraction, and is deflected at an angle with respect to the incoming beam direction. The properties of the light exiting the AOM can be controlled in five ways: (a) deflection angle, (b) intensity, (c) frequency, (d) phase, and (e) polarization. AOMs are much faster than typical mechanical devices, such as tiltable mirrors. The time it takes an acousto-optic modulator to alter the exiting beam is roughly limited to the transit time of the sound wave across the beam (typically 5 to 100 microseconds): this is sufficiently fast to create active modelocking in an ultrafast laser. Through careful design, transit times as low as a few hundred nanoseconds can be achieved. (It is noted that this represents the maximum time required to move the beam across the entire angular deflection range, and not the time necessary to deflect the beam from one angular position to one immediately adjacent to it. In other words, for specific applications, such as in the present invention, where the required sweeping is smooth across the scan range, considerably faster performance can be obtained than is the case for truly random-access deflection at an arbitrary angle. The only requirement is that there must be compensation for the amount of optical distortion potentially introduced into the light beam by the fast sweeping action by using a weak external optical element, such as a cylindrical lens.) AOMs offer fast response, good deflection range, simple solid-state design with no moving parts, and relatively low power consumption. Through the use of an AOM, a light beam is diffracted into several orders. By vibrating the material with a high-quality sinusoid and orienting the AOM to optimize deflection into the first diffraction order, up to 90% deflection efficiency can be achieved.

Use of the laser rastering technique described in co-pending U.S. patent application Ser. No. 11/934,277, incorporated in full herein by reference, in conjunction with the lysis-free single-dilution method of analyzing samples, will result in significant improvements in measurement rates. In the system of the present invention, a suitable deflection device is an acousto-optic deflector.

In the discussion that follows, the source of light is a laser. However, as stated previously, other sources of light can be used, such as, for example, lamps (e.g., mercury, xenon). Lasers include, but are not limited to, high-power water-cooled lasers (e.g., argon, krypton, dye lasers), low power air-cooled gas lasers (e.g., HeCd (UV), argon (488 nm), red HeNe (633 nm)); and solid-state and diode lasers (violet, blue, green, red). The laser beam is assumed to have a varying intensity profile, such as, for example, a Gaussian profile, in two directions.

Figure 5:
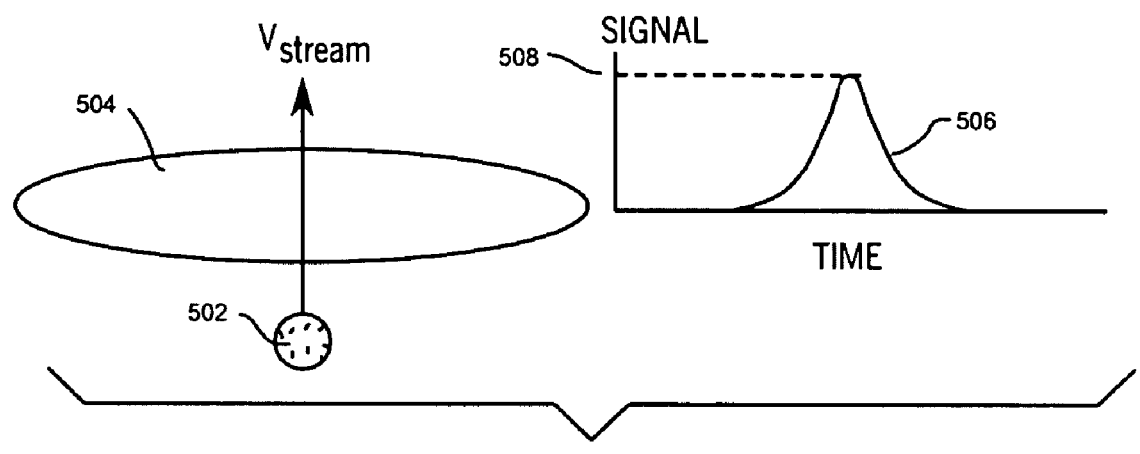
FIG. 5 is a schematic diagram illustrating the interaction of a cell with the laser beam in a conventional flow cytometer of the prior art, along with a graph indicating the conventional method of normalizing such an interaction by establishing and holding the peak value of the resulting signal.

Referring now to FIG. 5, in the prior art the cell 502 traverses the stationary light beam spot 504 as the cell 502 is carried along within the sample stream. As the cell 502 is exposed to portions of the beam spot 504 with varying intensity, the resulting amount of signal intensity 506 (initially in the form of scattered, or absorbed light, or emitted fluorescent light; and, after detection, in the converted form of electronic current or voltage) varies in accordance with the profile of the beam 504 in the direction (vertical in this depiction) traversed by the cell 502. In the prior art, this signal 506 is typically further detected by electronic circuitry that identifies the peak value 508 of the varying interaction between the light beam spot 504 and the cell 502 and stores it, typically in analog form, for subsequent digitization. This method of obtaining the value of interaction between a cell and a light beam is referred to in the prior art as "peak-and-hold."

Figure 6A:
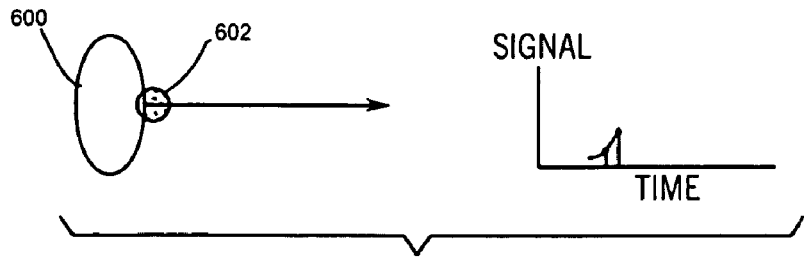
FIGS. 6A, 6B, 6C, 6D, and 6E are schematic diagrams, along with graphs, illustrating the interaction of a laser beam with a cell as the laser beam, which has a standard two-dimensional Gaussian profile, sweeps across the cell in the sample stream. In each of FIGS. 6A through 6E, inclusive, the graph positioned on the right of each diagram illustrates the value of the signal resulting from each interaction depicted, along with the values of the previous interactions.
Figure 6B:
Figure 6C:
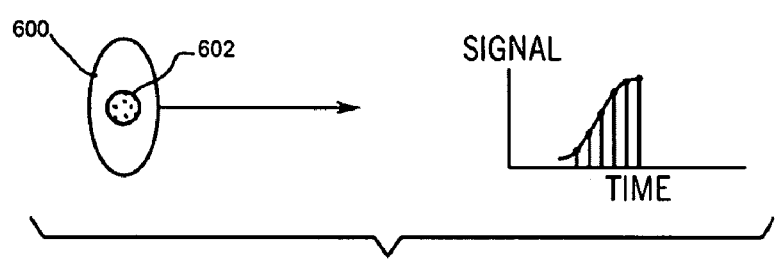
Figure 6D:
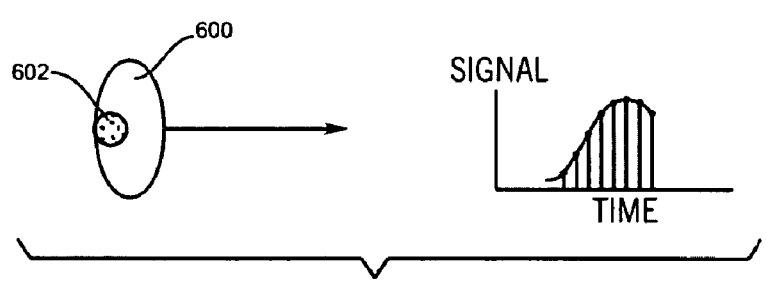
Figure 6E:
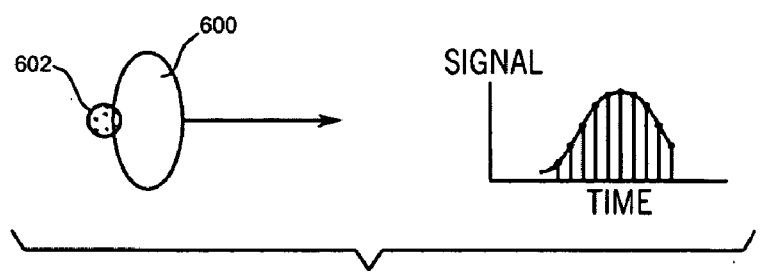
Figure 6F:
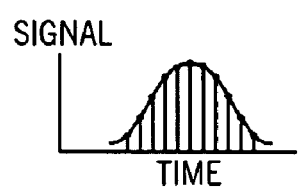
FIG. 6F indicates the intensity of the signal as a function of time, with representative values shown from the interactions illustrated in FIGS. 6A through 6E, inclusive.

Referring now to FIG. 3 for the method described herein, the beam is swept across the sample stream. As the beam is swept across the sample stream, each of the signals from the detectors (after suitable conditioning by circuitry described below) is sampled at a high frequency by an analog-to-digital converter (ADC). FIGS. 6A, 6B, 6C, 6D, and 6E show this process for the signal from one representative detector channel. These signals are generated by scattered or absorbed light or emitted fluorescent light. The digitized peak value of the series derived from the full interaction with a cell is stored for later use. FIGS. 6A, 6B, 6C, 6D, and 6E are schematic diagrams, along with graphs, illustrating the progressive interaction of a laser beam with a cell, as the laser beam, which has a standard two-dimensional Gaussian profile, sweeps across the cell in the sample stream. In these figures, the beam traverses the cell, while the position of the cell is essentially fixed (because the rate of flow of the cell in the sample stream is much lower than the rate of scanning by the beam). In each of FIGS. 6A through 6E, inclusive, the graph positioned on the right of each diagram illustrates the value of the digitized signal resulting from each interaction depicted, along with the values of the previous interactions. FIG. 6A shows the laser beam 600 making an initial contact with the cell 602. FIG. 6B shows the laser beam 600 significantly overlapping the cell 602. FIG. 6C shows the laser beam 600 centered on the cell 602, with the resulting interaction being at or near a maximum value. FIG. 6D shows the laser beam 600 significantly, but not maximally, overlapping the cell 602. FIG. 6E shows the laser beam 600 making one of its final contacts with the cell 602. FIG. 6F indicates the intensity of the signal as a function of time, with representative values shown from the interactions partially illustrated in FIGS. 6A through 6E, inclusive. The highest digitized value from this sequence, here depicted in FIG. 6C, is isolated from the rest of the values and stored either in working internal registers or in dynamic memory in the digital signal processing (DSP) module.

Figure 7A:
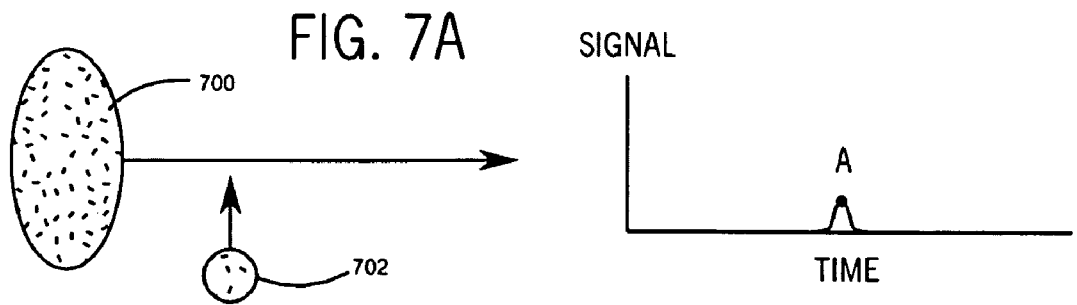
FIGS. 7A, 7B, 7C, and 7D are schematic diagrams, along with graphs, illustrating multiple successive interactions of a laser beam with a cell as the cell advances within the sample stream, and as the laser beam, which has a standard two-dimensional Gaussian profile, sweeps across the cell a plurality of times in consecutive raster scans. In each of FIGS. 7A through 7C, inclusive, the graph positioned on the right of each diagram illustrates the time-varying signals resulting from each interaction, along with the highest value of each signal.
Figure 7B:
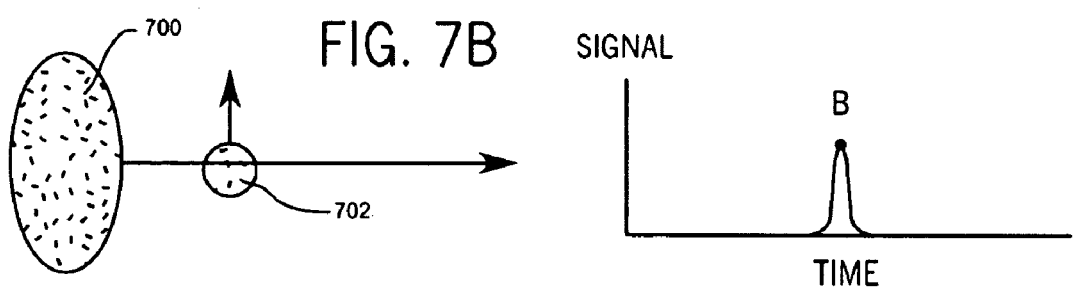
Figure 7C:
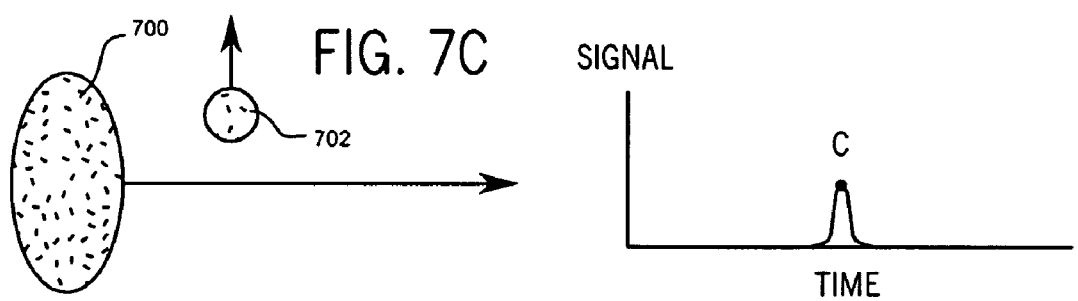
Figure 7D:
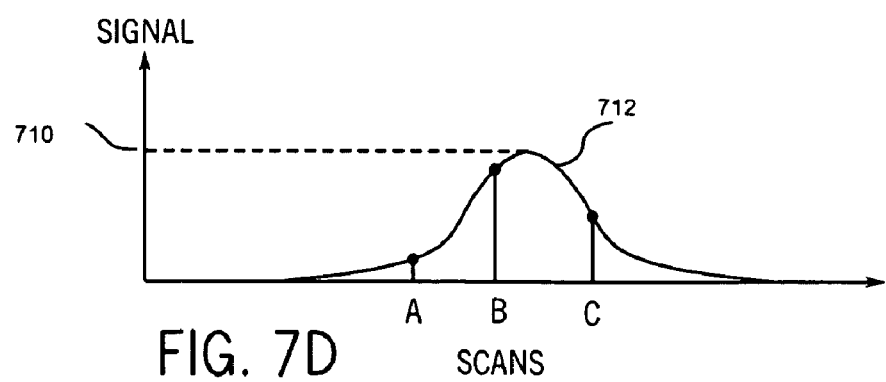

Next, as the laser beam scans the sample stream in successive sweeps, the light from the laser beam interacts with each individual cell a plurality of times, as shown in FIGS. 7A, 7B, and 7C. Each of these interactions results in a digitized peak value (for each detection channel), which is determined and stored as previously described. Because the interactions occur at different points on the beam profile, the interactions, in effect, sample the beam profile at discrete intervals—separated by the time taken to complete a single raster cycle. The DSP module collects the sequence of peak values from successive raster scans attributed to a single cell and correlates such sequence by at least one algorithm to the profile of the laser beam. The peak of the thus fitted curve is then further processed by downstream algorithms, as in a conventional instrument, for cell identification and counting. For example, FIG. 7A shows the result of an interaction wherein the laser beam 700 first contacts a cell 702. FIG. 7B shows the result of the subsequent interaction, during the immediately following raster scan, wherein the same cell 702 as in FIG. 7A has advanced further in the sample stream and interacts relatively close to the central portion of the laser beam 700. FIG. 7C shows the result of a third subsequent interaction, during the following raster scan, wherein the same cell 702 as in FIGS. 7A and 7B has advanced further in the sample stream and interacts with the shoulder of the laser beam 700. FIG. 7D shows schematically the process of arranging the peak values A, B, C from the interactions depicted in FIGS. 7A, 7B, and 7C, respectively, into a sequence ordered by scan number; and the additional process of extracting from such an ordered sequence the inferred peak value 710, by adapting (via at least one algorithm, at least one mathematical expression, or at least one electronic technique, or any combination of the foregoing) to the sequence a curve 712 representing the expected shape of the interaction, such shape depending mainly on the profile of the laser beam 700 in the vertical direction, particularly the width of the laser beam 700. The rastering frequency, the width of the sample stream, and the velocity of the sample stream must be set so that each cell is intercepted a plurality of times as it flows past the beam of light.

Figure 8A:
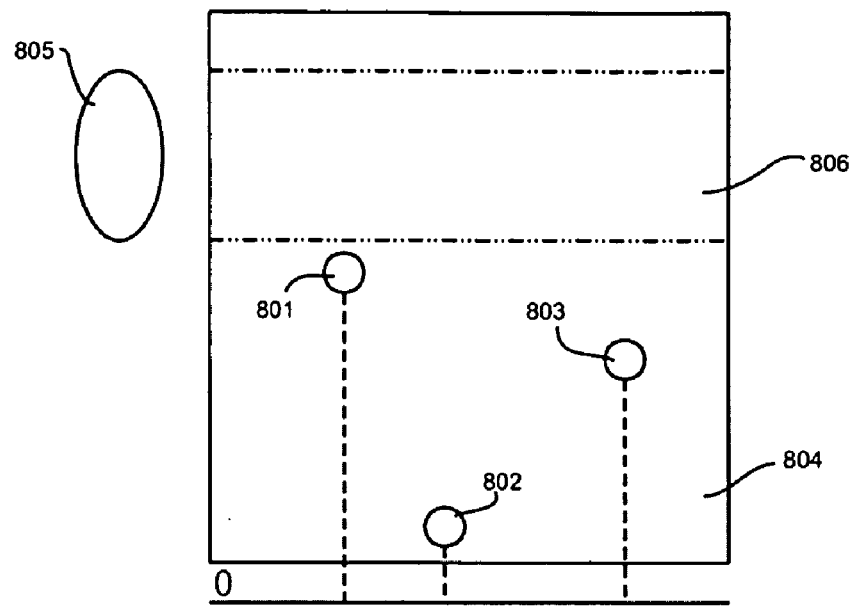
FIGS. 8A, 8B, 8C, 8D, 8E, 8F, 8G, 8H, 8I, 8J, 8K, 8L, and 8M comprise a series of schematic diagrams illustrating the spot of a laser beam interacting with several cells moving in a sample stream. Below each diagram is shown the signal, from a representative detector, resulting from each such interaction, which signal is displayed in ordered sections corresponding to each successive raster scan.
Figure 8B:
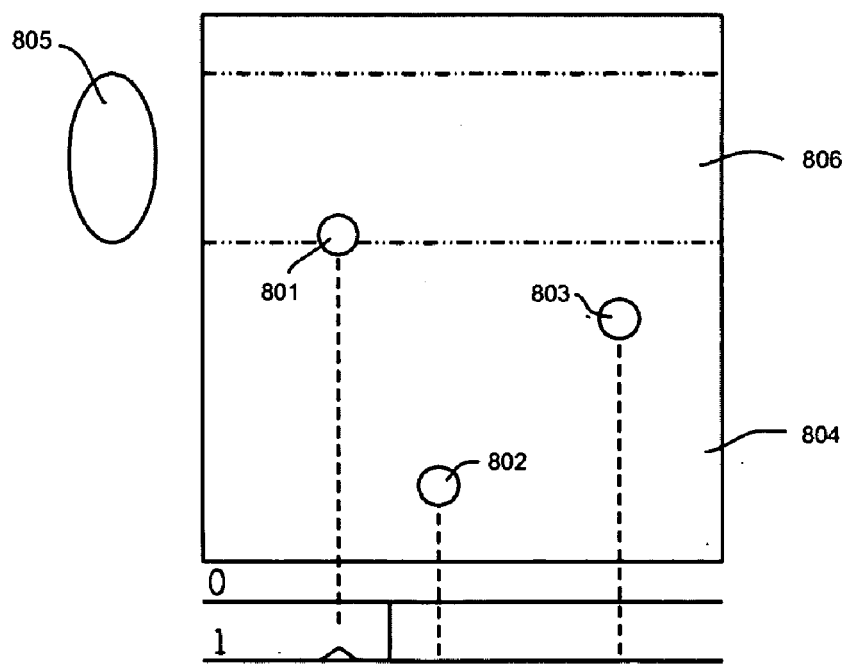
Figure 8C:
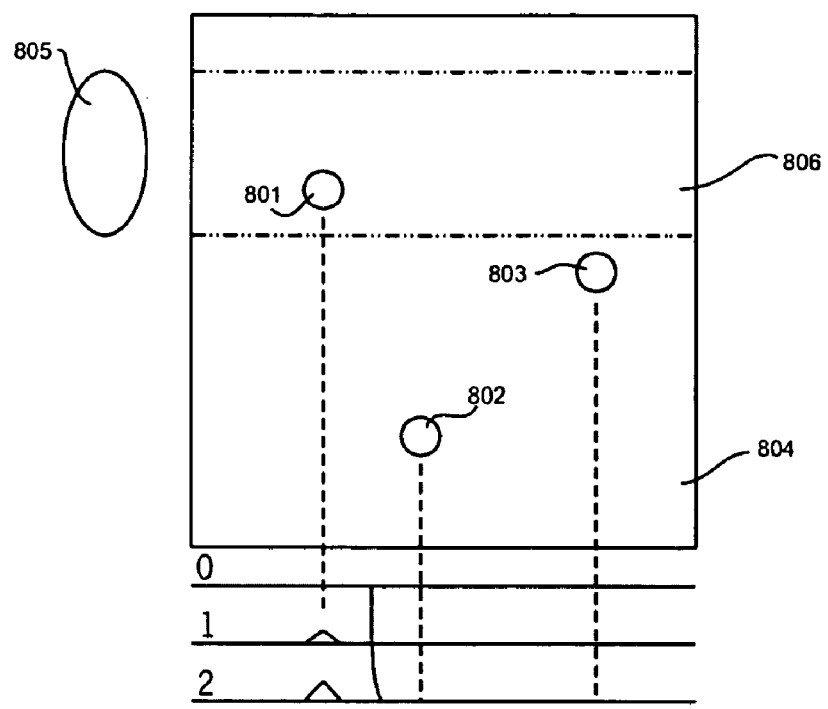
Figure 8D:
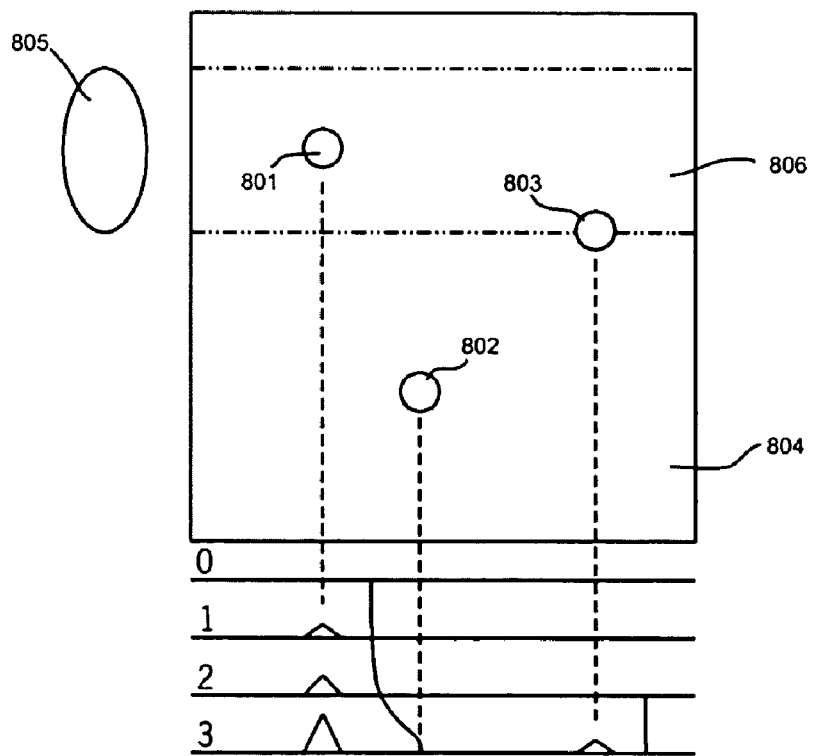
Figure 8E:
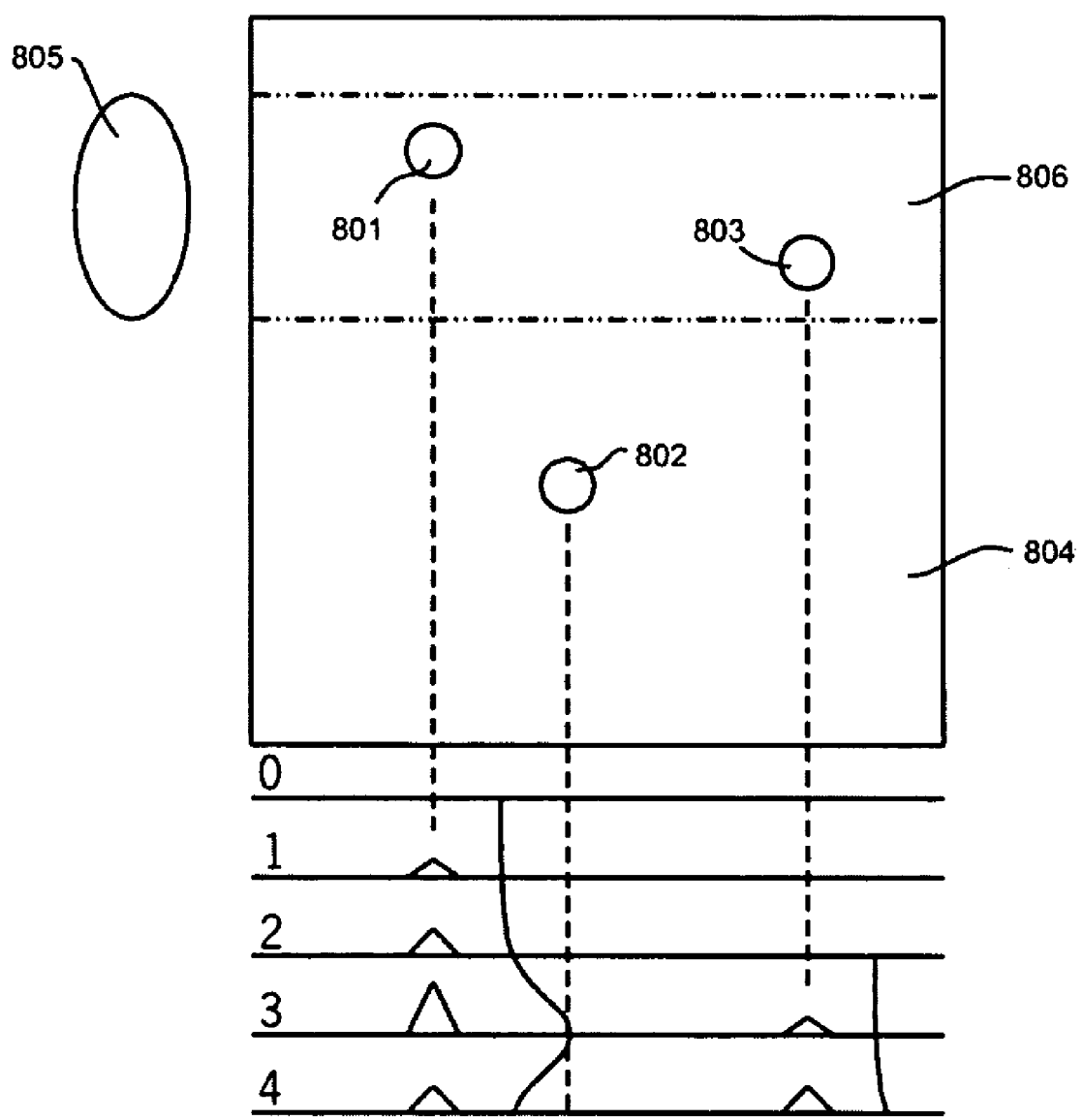
Figure 8F:
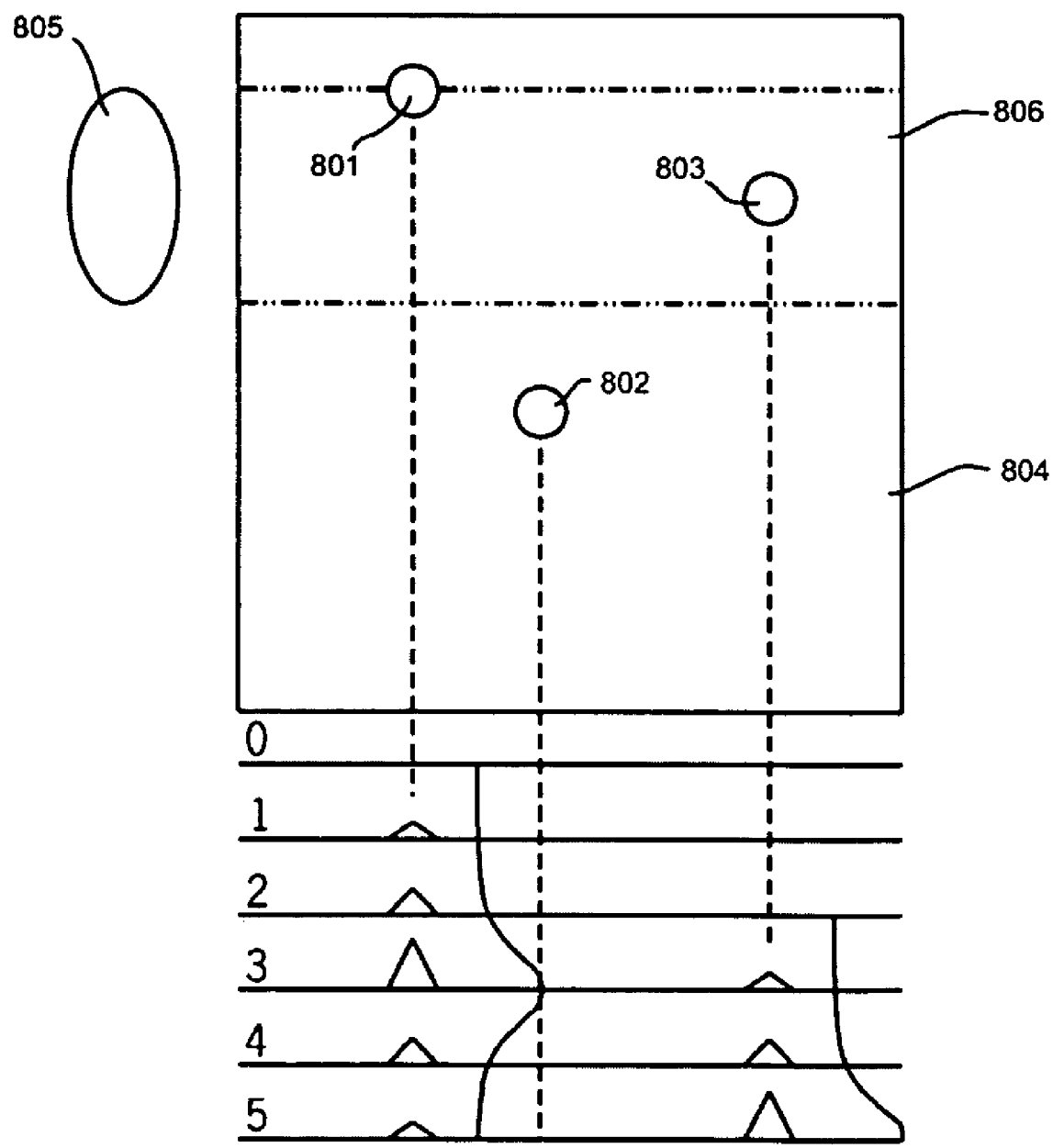
Figure 8G:
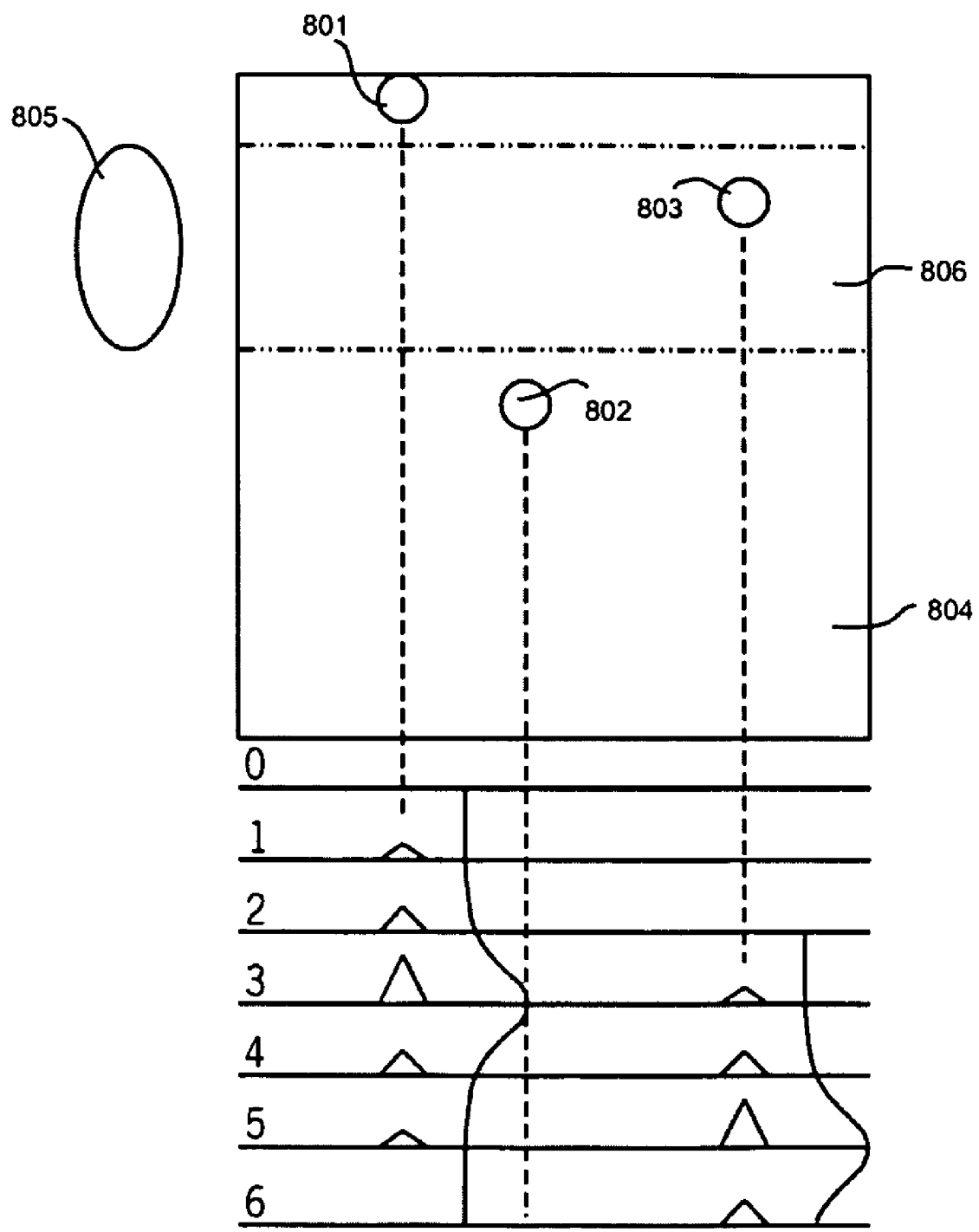
Figure 8H:
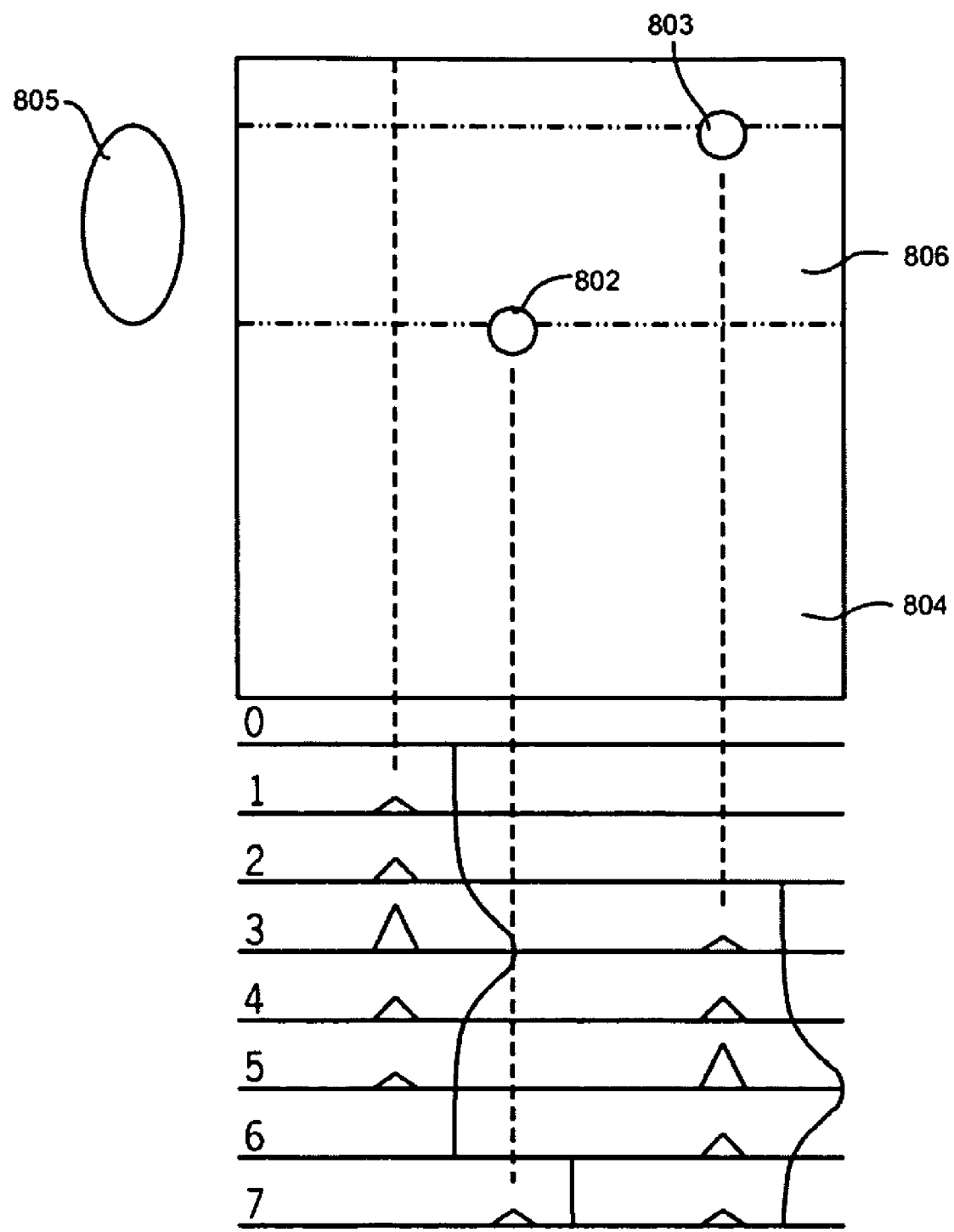
Figure 8I:
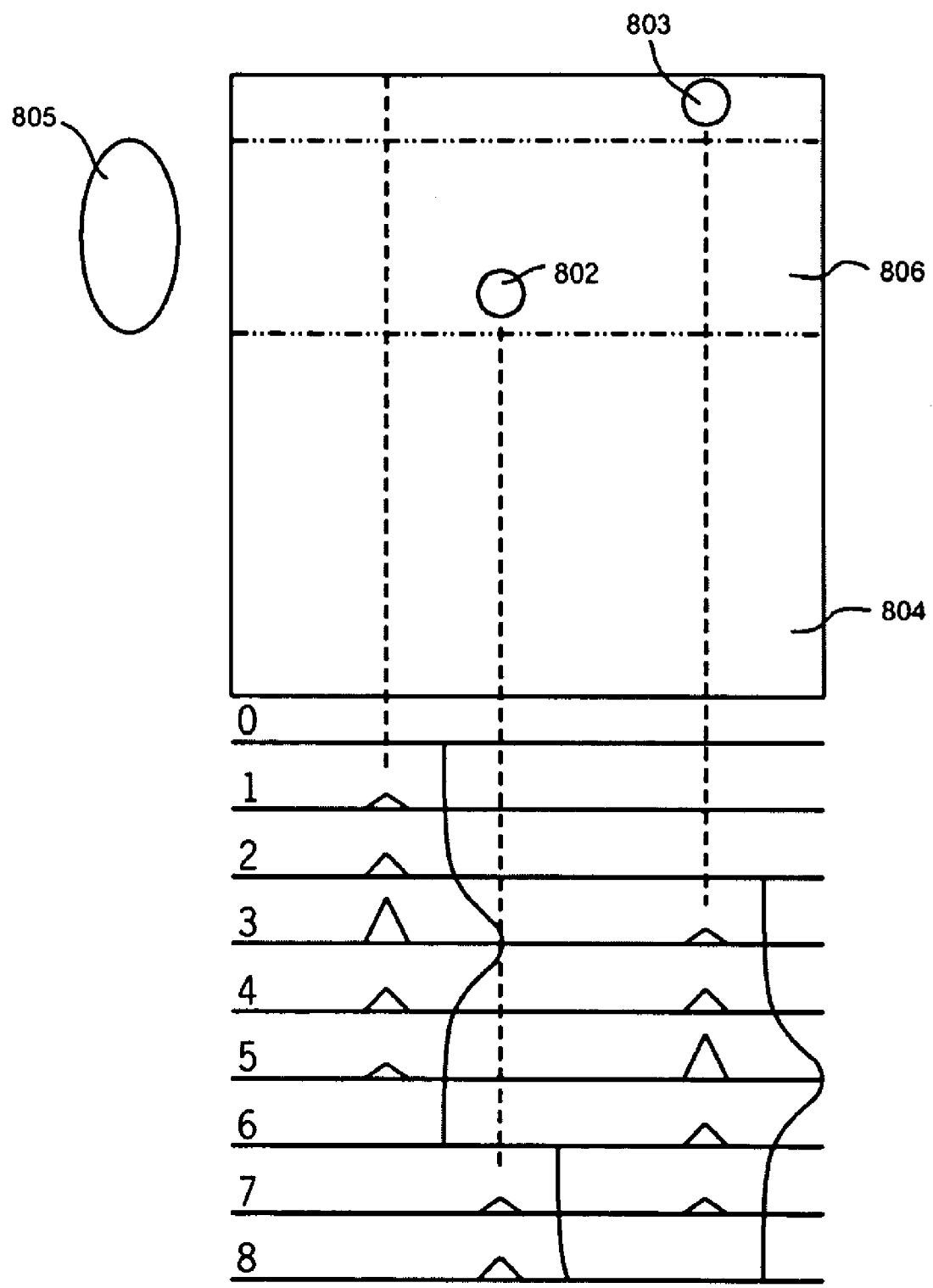
Figure 8J:
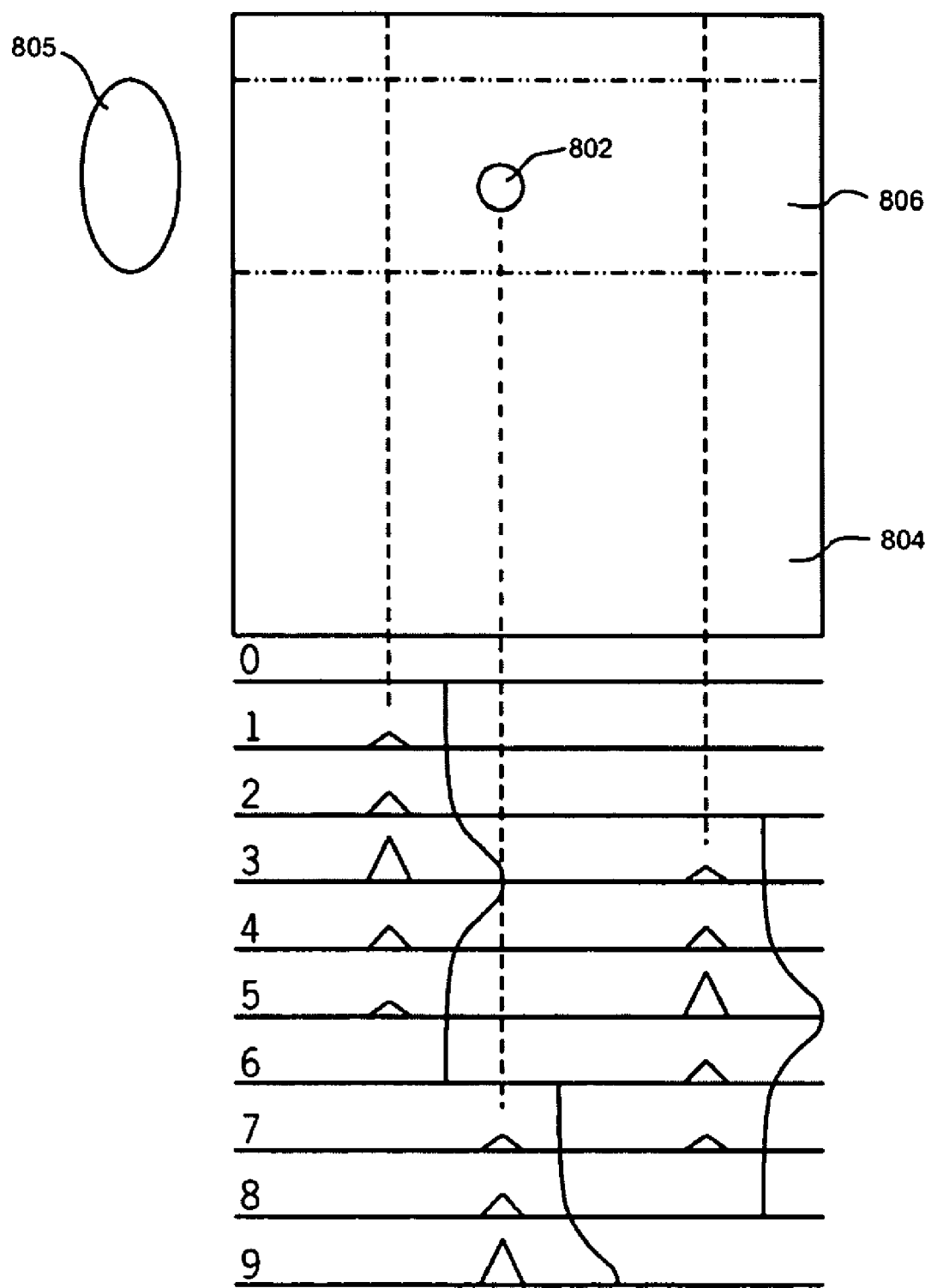
Figure 8K:
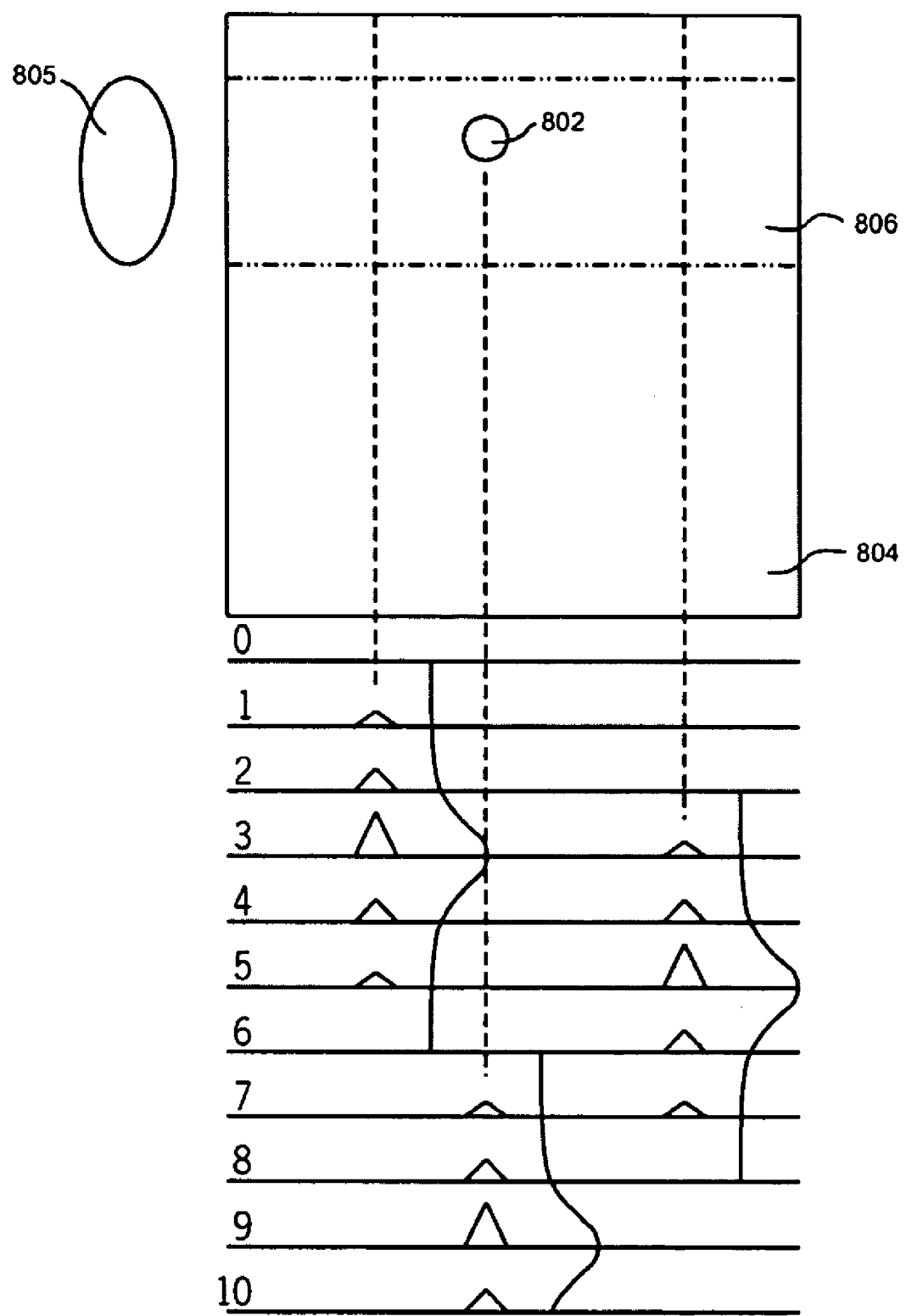
Figure 8L:
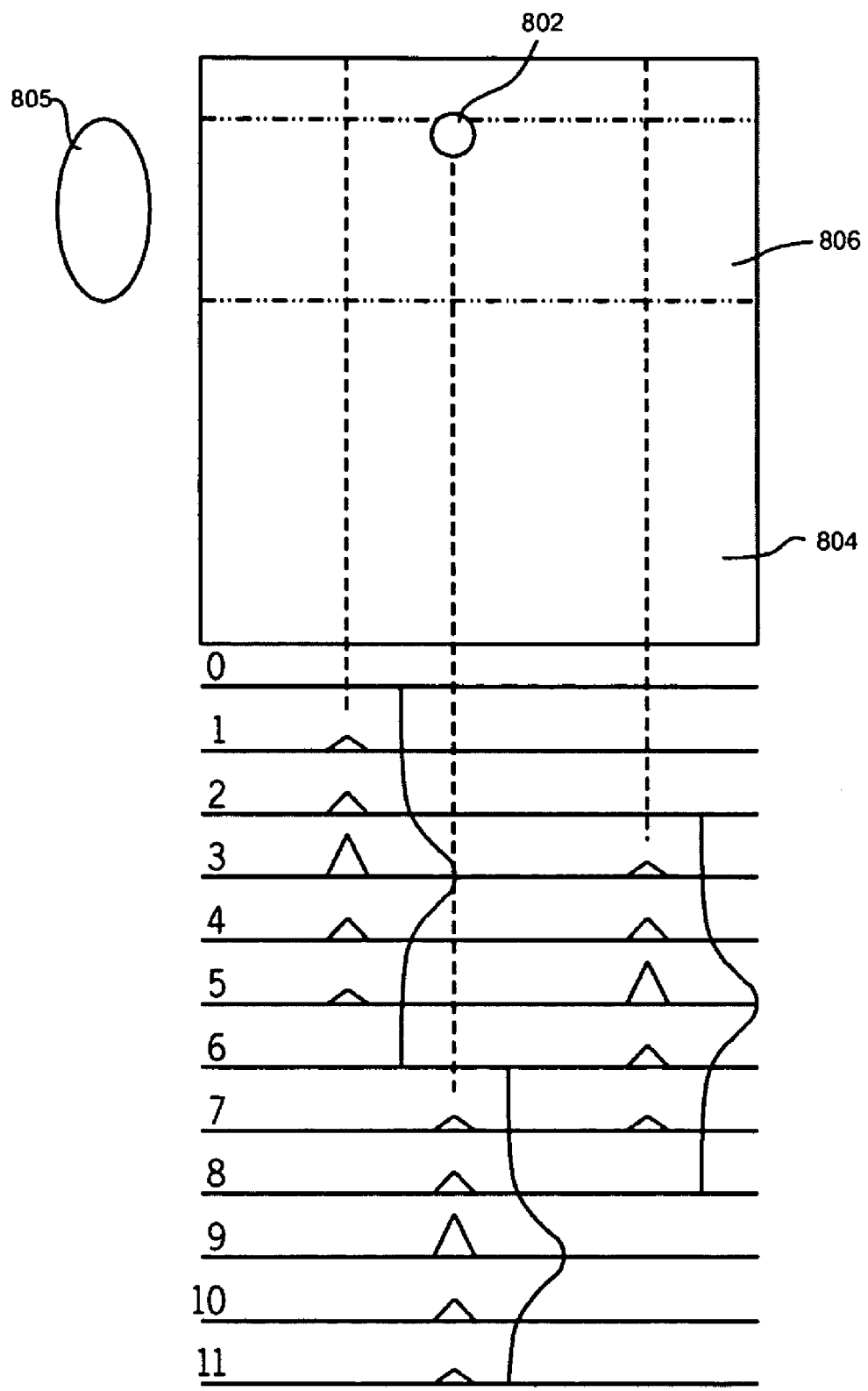
Figure 8M:
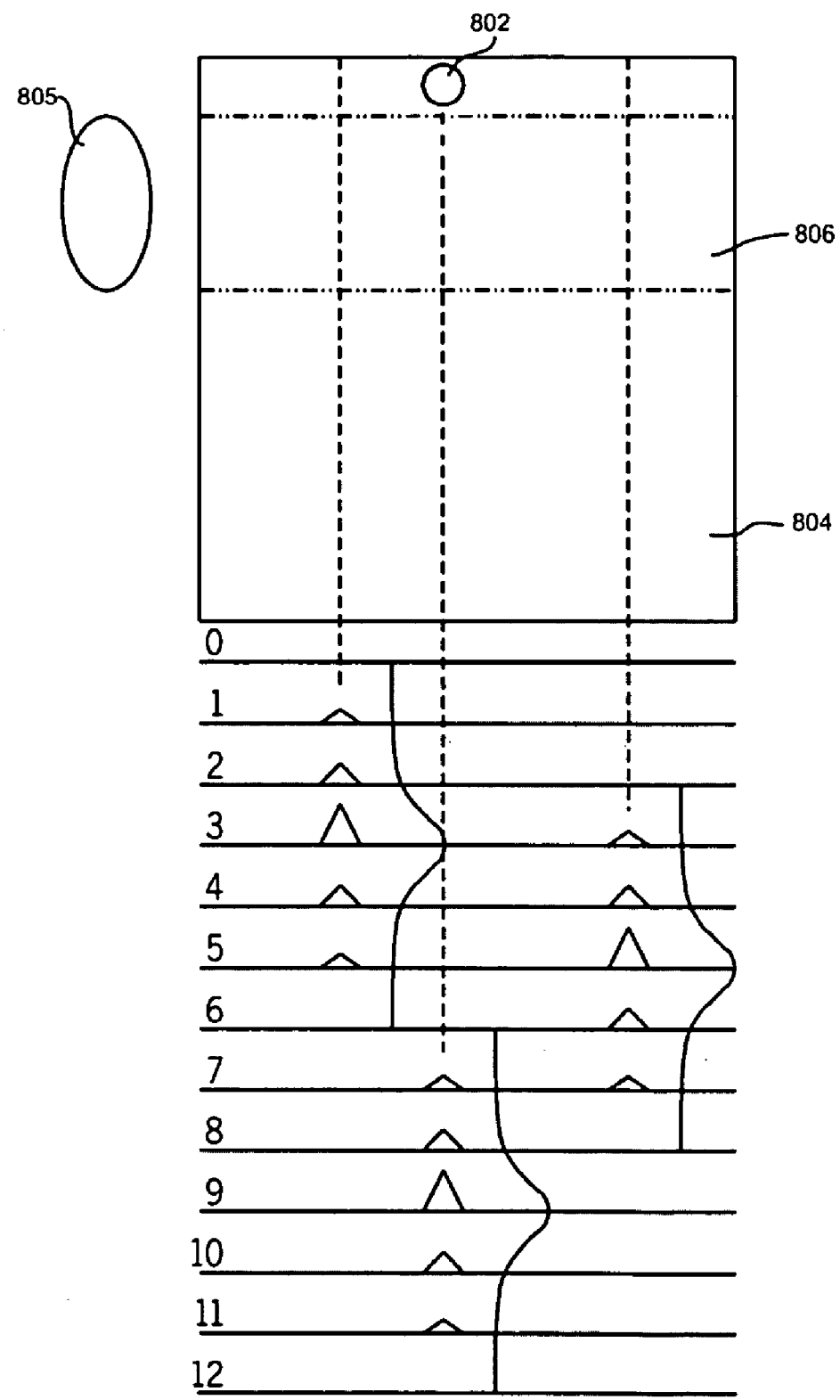

A depiction of the laser rastering method described herein, but with a plurality of cells to illustrate how the measurement rate is increased without increasing coincidences, can be seen in FIGS. 8A, 8B, 8C, 8D, 8E, 8F, 8G, 8H, 8I, 8J, 8K, 8L, and 8M. FIGS. 8A through 8M, inclusive, illustrate the movement of three cells 801, 802, and 803 moving within a sample stream 804. The cell 801 is ahead of the cell 803 by a slight distance in the sample stream 804; the cell 801 is ahead of cell 802 by a greater distance in the sample stream 804. The cells 801, 802, and 803 are moving upwardly. The cells 801, 802, and 803, which are merely just three of the cells in the sample stream 804, are illuminated by a beam of light 805, which is rastered, i.e., is swept from side to side, by a deflection device, such as, for example, an AOD. The sweeping movement of the beam describes a band 806, in sample stream 804, where cells are illuminated by the light beam at some point in the course of each raster scan. The series of horizontal lines 0 through 12, inclusive, below the sample stream 804, illustrates the sequence of varying signals (taken, for example, directly at the output of a representative detector channel) generated by each cell, or a plurality of cells, at a well-defined point in each scan. For example, during scan 0 (FIG. 8A), none of the cells 801, 802, 803 have interacted with the beam 805 in the region 806. Line 0 indicates the lack of a signal peak. During scan 1 (FIG. 8B), the cell 801 interacts with a low-intensity portion of the beam 805, but the cells 802 and 803 have not yet interacted with the beam 805. Line 1 indicates a low signal peak for the interaction of the beam 805 with the cell 801. During scan 2 (FIG. 8C), the cell 801 interacts with a portion of the beam 805 that is intermediate to the low-intensity portion of the beam 805 and to the high-intensity portion of the beam 805, but the cells 802 and 803 have not yet interacted with the beam 805. Line 2 indicates a higher signal peak for the interaction of the cell 801 with the beam 805 than was observed during scan 1 (Line 1). During scan 3 (FIG. 8D), the cell 801 interacts with a high-intensity portion of the beam 805, the cell 803 interacts with a low-intensity portion of the beam 805, but the cell 802 has not yet interacted with the beam 805. Line 3 indicates the signal peaks for the interaction of the beam 805 with the cell 801 (highest signal peak, at left, for the cell 801) and with the cell 803 (low signal peak, at right, for the cell 803). During scan 4 (FIG. 8E), the cell 801 interacts with a portion of the beam 805 intermediate to the high-intensity portion of the beam 805 and to the low-intensity portion of the beam 805, the cell 803 interacts with a portion of the beam 805 that is intermediate to the low-intensity portion of the beam 805 and to the high-intensity portion of the beam 805, but the cell 802 has not yet interacted with the beam 805. Line 4 indicates the signal peaks for the interaction of the beam 805 with the cell 801 (intermediate signal peak for the cell 801) and with the cell 803 (intermediate signal peak for the cell 803). Table 1 summarizes the results of the aforementioned interactions of the cells 801, 802, and 803 and the remaining interactions of the cells 801, 802, and 803 with the beam 805 across the region 806 up to the point where the cell 802 departs the region 806 of illumination by the beam 805. It should be noted that FIGS. 8A, 8B, 8C, 8D, 8E, 8F, 8G, 8H, 8I, 8J, 8K, 8L, and 8M depict schematic, not actual, interactions of the cells with the beam. In Table 1, there are four types of interactions depicted: (a) no interaction, when no part of the beam 805 intersects a cell; (b) low signal peak, when a low-intensity portion of the beam 805 intersects a cell; (c) high signal peak, when a high-intensity portion of the beam 805 intersects a cell; and (d) intermediate signal peak, when the cell intersects a portion of the beam 805 that is intermediate to the low-intensity portion of the beam 805 and to the high-intensity portion of the beam 805. These four types of interactions are also intended to be schematic and do not imply that only four distinct levels of interaction can result from the apparatus and method disclosed herein; indeed, the interactions can take any of a very large set of values, depending on, for example, the relative sizes of cells, the intensity of the laser beam, and the presence and degree of noise (whether optical, biological, or electrical) in the system.

TABLE 1

| Scan no. (FIG. no.) | Character of signal peak based on intersection of the cell 801 with the beam 805 in region 806 | Character of signal peak based on intersection of the cell 802 with the beam 805 in region 806 | Character of signal peak based on intersection of the cell 803 with the beam 805 in region 806 |
|---|---|---|---|
| 0 (8A) | none | none | none |
| 1 (8B) | low | none | none |
| 2 (8C) | intermediate | none | none |
| 3 (8D) | high | none | low |
| 4 (8E) | intermediate | none | intermediate |
| 5 (8F) | low | none | high |
| 6 (8G) | none | none | intermediate |
| 7 (8H) | none | low | low |
| 8 (8I) | none | intermediate | none |
| 9 (8J) | none | high | none |
| 10 (8K) | none | intermediate | none |
| 11 (8L) | none | low | none |
| 12 (8M) | none | none | none |

The sequence shown in FIGS. 8A through 8M, inclusive, constitutes a discrete sampling of the profile of the beam of the source of light 805. Correlation (by fit, filtering, other algorithm, or dedicated electronic circuit) of the sampled interactions with a curve representing the profile of the light beam in the vertical direction occurs in real time on, and in the immediate vicinity of, all the points along the digitized raster scans, where there is a non-zero peak. Such points are diagrammatically indicated by the dashed lines in FIGS. 8A through 8M, inclusive. Accordingly, each separate sequence of detected peaks belonging to a single cell can be fit to a representation of that profile. By using the technique of rastering described herein, the cells 801, 802, and 803 can be distinguished from one another, even though two or more of them may pass through the illumination region 806 simultaneously (or in partial simultaneity, as depicted in FIGS. 8A through 8M by cells 801 and 803, and separately by cells 803 and 802), because the cells interact with the beam 805 at different points of each raster scan. Accordingly, the technique of rastering enables a flow cytometer to analyze a greater number of cells per unit time, while the number of coincidences can be maintained at an acceptably low level.

The processing of the signals, from each detector, following the interactions illustrated in FIGS. 8A through 8M, is depicted schematically in FIG. 9. The block diagram 900 shows a collection of detectors 902, 904, . . . (two detectors are shown as representative of an optionally larger set). Each detector is connected to a separate preamplifier circuit 912, 914, . . . (again, two preamplifier circuits are shown as representative of an optionally larger set commensurate with the number of detectors used). The preamplifier circuits for the various detectors may physically reside on the same electronic submodule, or they may be partitioned according to electrical requirements (such as, for example, noise isolation, voltage supply requirements, physical proximity to the detector, etc.) pertaining to each detector, or some portion of them may be combined and some portion kept separate. The signals from each detector so amplified by each preamplifier circuit then progress through an analog signal-conditioning submodule 920. The functions of this submodule include reduction or elimination of dc or quasi-dc offsets from each of the signals (a process also known as baseline restoration), partial or complete compensation of nonuniformities in the intensity of the light delivered to the flowcell as a function of position along the raster scan (a process also known as AOD intensity compensation), and optionally filtering to reduce or remove, for example, high-frequency noise from each of the signals. The signals in each channel so conditioned then proceed to the analog-to-digital converter (ADC) submodule 930, where each signal channel has a dedicated ADC channel clocked at high frequency (at the level of 100 million samples per second, MS/s, for each channel) and sufficient resolution (about 14 bits). The function of the ADC submodule 930 is to convert the analog signals in each channel of detection into digitized values and discrete, but closely spaced, time intervals, as shown, for example, in FIG. 6F. The signals so digitized then progress to the digital signal processing (DSP) submodule 940. This submodule 940 can comprise either a single powerful field-programmable gate array (FPGA) 942, or a DSP chip 944; or, optionally, a plurality of FPGAs or DSP chips, or both a FPGA and a DSP chip, or a plurality of FPGAs and a plurality of DSP chips, depending on the speed and computational requirements of the specific application of the analyzer in which they are incorporated. Additionally, submodule 940 preferably comprises: (a) random access memory (RAM) units 946 for optional intermediate storage of data for computation, for staging data before transmission over a data bus or other means of conveyance to the next stages of processing, or for both intermediate and staging data storage; and (b) a digital-to-analog converter (DAC) unit 948 that takes inputs from the FPGA(s) 942, the DSP(s) 944, or both the FPGA(s) 942 and the DSP(s) 944 and converts them into analog signals. These analog signals are used to dynamically, or programmatically, alter the operating parameters (e.g., supply voltage) of portions or a totality of the detectors 902, 904, . . . ; the operating parameters (e.g., gain settings) of the preamplifier submodules 912, 914, . . . ; the operating parameters (e.g., amount of dc or quasi-dc offset) of the analog submodule 920; or a combination of operating parameters of detectors, preamplifiers, and analog submodule. The functions of the DSP submodule 940 are to: (a) select the highest digitization value from a cell interaction during a single raster scan (or a plurality of such values, if more than a single cell is present during a single raster scan as shown, for example, in FIG. 8E); (b) to optionally apply a known factor to the values thus identified, based on their position along the raster scan, in order to effect any necessary residual AOD intensity compensation not already executed in the analog submodule 920; (c) to correlate such highest values across successive raster scans in order to reconstruct the peak value of the interaction between each cell and the laser beam spot (as illustrated in, for example, FIGS. 7D and 8M); (d) to apply programmatically predetermined numerical upper, lower, or upper and lower, thresholds, specific to each channel of detection, to the peak values so reconstructed in order to select out of the population of detected events those that, within a particular assay, are most likely to represent the population of interest, and to reject or differently classify the remainder; and (e) to coordinate the information thus constructed and filtered, coming from each individual channel of detection, into a digital entity (typically referred to as one element of a "listmode" file) that contains time-stamp information as well as the reconstructed values from each of the channels of detection involved in the measurement pertaining to that same individual cellular transit event. The collection of listmode events is then collated into one or a plurality of listmode batches, which can be temporarily stored, e.g., in RAM units 946. The batches of data can then be periodically transferred (from the RAM units 946, or directly from the FPGA 942, or directly from the DSP chip 940, if present; and through appropriate data channels, such as, for example, a Peripheral Component Interconnect (PCI) bus), at times determined by means of a program, to the operating system of the analyzer (AOS) 950 for further processing by algorithms, such as, for example, algorithms for identifying cells, counting cells, and flagging cells. The DSP submodule 940 can optionally incorporate the ADC submodule 930, and can also optionally incorporate the analog submodule 920.

The apparatus and method described herein provides an instrument that maintains satisfactory performance with respect to precision, coincidences, and signal-to-noise ratio. The method of the present invention allows selection of rastering speeds and flow stream parameters to conform to the desired digitization frequency and to allow multiple scans over a single cell. The present invention can be implemented with commercially available components (e.g., AOD, ADC, FPGA). The apparatus and method described herein can provide a substantial improvement in the measurement rate (cells analyzed per second). This improvement results in: (a) a reduction in the time required to perform a standard CBC, thereby yielding a higher throughput (CBC/hr); (b) an increase in the total number of cells analyzed per sample run, thereby yielding higher statistical precision in the determination of, in particular, the existence, the concentration, or the existence and the concentration of relatively rare cellular events; or (c) a combination of both a higher throughput and an increase in the number of total cells analyzed. In addition, the apparatus and method described herein provides a significant reduction in the complexity of the analyzer, in the number of separate processing steps required for a standard CBC, in the number and amount of reagents used to obtain a CBC, in the cost of its manufacture, in the risk of failure during operation, and in the cost of maintenance and service. Furthermore, the apparatus and method described herein eliminates the need to lyse RBCs during the WBC assay, thereby eliminating the interference with the WBC count or differential assay from lyse-resistant RBCs (including, e.g., sickle cells, target cells, and RBCs from neonates).

The conditional constraints of the present invention are summarized by the

1 (peak signal strength): $\frac{P'_{laser}}{w'_{ox}w'_{oy}} \geq \frac{P_{laser}}{w_{ox}w_{oy}}$

2 (integrated signal strength): $\frac{P'_{laser}}{w'_{oy}x'_{stream}f'_{raster}} \geq \frac{P_{laser}}{w_{ox}v_{stream}}$

3 (coincidences): $\rho' w'_{ox} w'_{oy} z'_{stream} \leq \rho x_{stream} w_{oy} z_{stream}$

4 (multiple digitizations over cell): $\frac{w'_{ox} f'_{digitization}}{x'_{stream} f'_{raster}} \geq 10$

5 (digitization constraint): $f'_{digitization} \leq 125\,\text{MHz}$

6 (multiple raster scans over cell): $\frac{w'_{oy} f'_{raster}}{v'_{stream}} \geq 3$

7 (rastering constraint): $f'_{raster} \leq 1\,\text{MHz}$

8 (measurement rate requirement): $\rho' x'_{stream} z'_{stream} v'_{stream} \geq$ $\rho x_{stream} z_{stream} v_{stream}$ following mathematical relationships:
where
$P_{laser}$ represents the laser beam power,
$w_{ox}$ and $w_{oy}$ represent the dimensions of a focused spot (i.e., at or near the waist) of a laser beam (horizontal and vertical, respectively),
$x_{stream}$ and $z_{stream}$ represent the dimensions of the sample stream (width and depth, respectively),
$v_{stream}$ represents the velocity of the sample stream,
$f_{digitization}$ represents the digitization frequency, $f_{raster}$ represents the frequency of repetition of the raster scans, and where the parameters represented by primed symbols indicate the parameter values in the apparatus and method described herein, and the parameters represented by unprimed symbols indicate the parameter values in the prior art. As used herein, the expression "conditional constraint" means a value expressed as a mathematical relationship for establishing target operating conditions for a flow cytometry apparatus and method. It is to be understood that such constraints are only broadly indicative of the ultimate operating conditions selected for implementation, such as, for example, constraints attributable to technological limitations, such as the speed of electronic components, which can be relaxed by the introduction of improved devices. Also, other constraints may represent the absolute minimum requirement for a particular operating parameter, wherein good engineering design considerations would suggest adoption of a value of such a parameter with a margin of tolerance for manufacturing, operating, and specimen variabilities.

Turning to the signal strength parameters, condition #1 (peak signal strength) is defined by the following relationship:

$$\frac{P'_{laser}}{w'_{ox}w'_{oy}} \geq \frac{P_{laser}}{w_{ox}w_{oy}} \qquad \text{condition \#1}$$

This relationship states the requirement for the (average) photon flux, or intensity of the beam, at the cell: the smaller the beam spot, the higher the intensity for a given power. Whereas the signal processing system primarily records the peak height of the resulting signal as the parameter of interest (which is widespread practice in the prior art for the handling of scattering signals), in order to ensure that the peak signal strengths are comparable to those in the prior art, condition #1 states that, for a smaller beam spot, a proportionately lower laser power will suffice.

Condition #1 is to be compared to condition #2 (integrated signal strength), where another relationship applies:

$$\frac{P'_{laser}}{w'_{oy}x'_{stream}f'_{raster}} \geq \frac{P_{laser}}{w_{ox}v_{stream}} \qquad \text{condition \#2}$$

This relationship reflects the fact that, where the time-integrated signal is the recorded parameter of interest (as is the case in some instances of the prior art for scattering signals, and more generally the case in the prior art for fluorescence signals), the relevant quantities include not only the intensity of the light beam at the cell, but also the length of time the beam interacts with the cell. In a laser rastering system, the generally smaller beam spot yields a higher intensity, as compared with the prior art (automatically satisfying condition #1 if the laser power is unchanged), but the relatively shorter time of interaction could yield a lower integrated signal, even though the average beam intensity is higher. Thus, if integrated signals are required, a somewhat higher laser power may be necessary to maintain parity with the corresponding signals from a system of the prior art that does not employ rastering.

Figure 10:
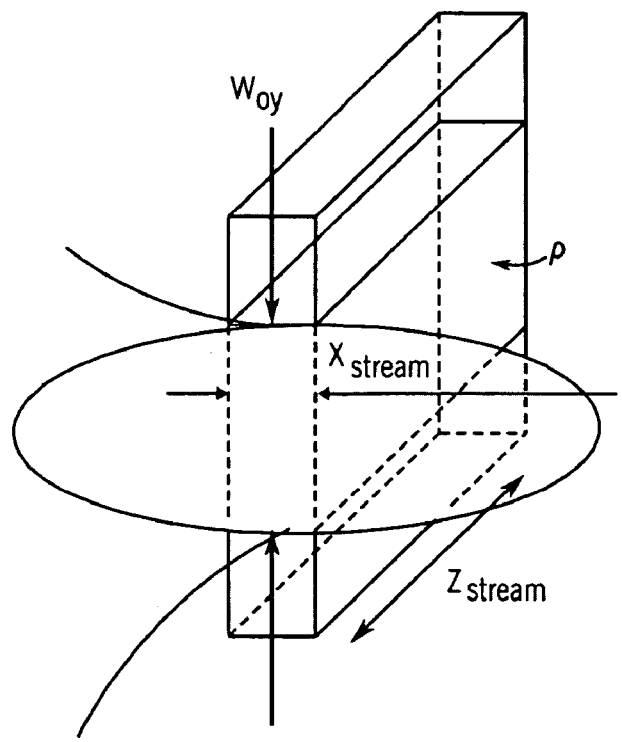
FIG. 10 is a schematic diagram of a volume of sample illuminated at any one time by a laser beam of the prior art.
Figure 11:
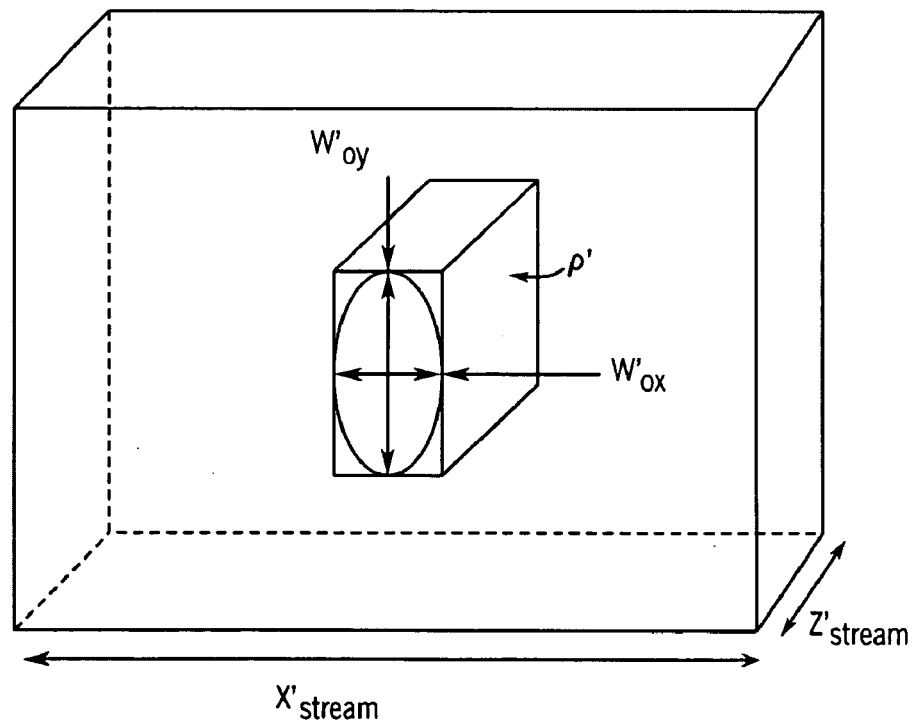
FIG. 11 is the analogue of FIG. 10 for the method described herein.

Turning now to the coincidences parameter, FIG. 10 shows diagrammatically an approximate illuminated volume of the prior art, and FIG. 11 shows diagrammatically an approximate illuminated volume encountered in the present invention. The following two relationships provide the parameters utilized to determine the number of cells in the volume illuminated at any instant of time. The term "current" refers to the prior art. The term "new" refers to the present invention.

$N_{cells} = \rho x_{stream} w_{oy} z_{stream}$ current number of cells in illuminated volume $N'_{cells} = \rho' w'_{ox} w'_{oy} z'_{stream}$ new number of cells in illuminated volume In the prior art, the cell concentration ρ depends on the assay. It is highest for a RBC and platelet assay (see, for example, the CELL-DYN® Sapphire®, where the dilution ratio for such assay is 1:290) and lowest for a WBC assay (where the dilution ratio is 1:35, but where the relatively very numerous RBCs and platelets have been excluded using a combination of biochemical and electronic rejection means). In the apparatus and method described herein, there is a single dilution, with concentrations of the different cell populations proportionate to their undiluted concentrations in human whole blood. For the purpose of estimating coincidence levels, however, the population that matters the most is the most numerous; it is the concentration of this population to which the quantity ρ' refers. With these conventions, condition #3 (coincidences) can be defined by the following relationship:

$$\rho' w'_{ox} w'_{oy} z'_{stream} \leq \rho x_{stream} w_{oy} z_{stream} \qquad \text{condition \#3}$$

Figure 12A:
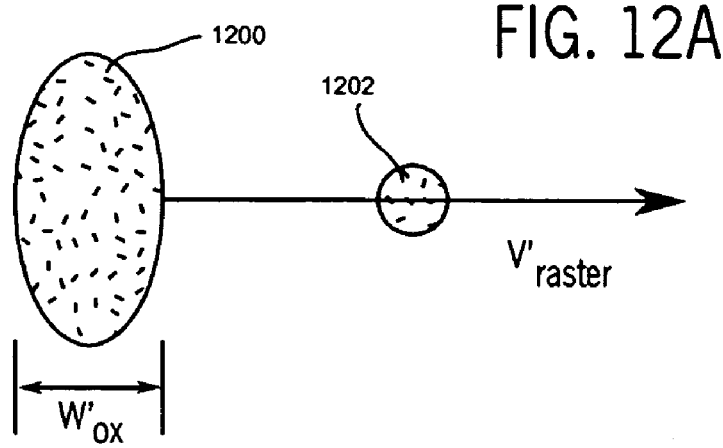
FIGS. 12A, 12B, and 12C are schematic diagrams illustrating the laser beam interacting with a cell.
Figure 12B:
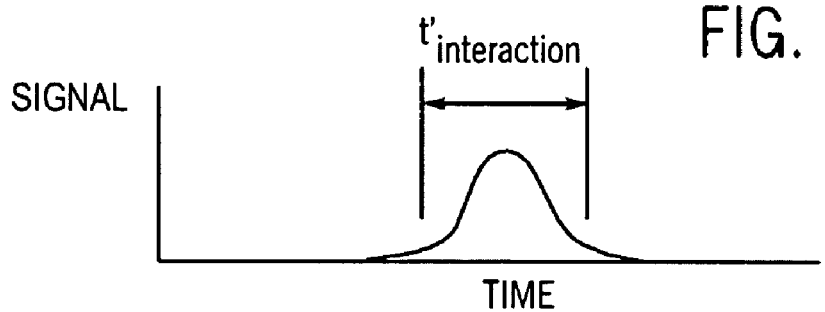
Figure 12C:
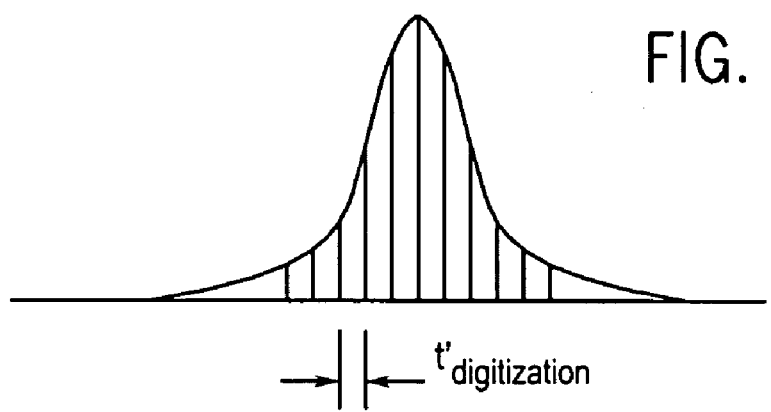

Turning now to the digitizations parameter, FIG. 12A shows diagrammatically the interaction of a laser beam spot 1200 with a cell 1202. FIG. 12B shows a hypothetical plot of signal intensity as a function of time. FIG. 12C shows a hypothetical plot of digitizations developed by an analog-to-digital converter. Based on the following relationships, i.e.:

$$t'_{interaction} = \frac{w'_{ox}}{v'_{raster}}$$

$$= \frac{w'_{ox}}{x'_{stream} f'_{raster}} \qquad \text{interaction time}$$

$$t'_{digitization} = \frac{1}{f'_{digitization}} \qquad \text{digitization time}$$

condition #4 (multiple digitizations over cell) can be defined by the following relationship:

$$\frac{w'_{ox} f'_{digitization}}{x'_{stream} f'_{raster}} \geq 10 \qquad \text{condition \#4}$$

where the number 10 is selected to nominally indicate the approximate number of digitizations required to capture with sufficient accuracy the varying profile of the signal from interaction between the laser beam and a cell in the course of any single raster scan.

For condition #5 (digitization constraint), the mechanism of ADCs is such that a trade-off relationship exists between the digitization frequency and the depth of resolution. The fastest commercially available analog-to-digital converters can digitize with 14-bit resolution at 125 MHz or with 16-bit resolution at 100 MHz. For the purpose of the apparatus and method described herein, a 14-bit resolution is adequate, while the highest possible frequency of digitization is desired. Therefore, $$f_{digitization} \leq 125 \text{ MHz} \qquad \text{condition \#5}$$

where the condition is meant to indicate the constraint imposed by the performance of currently available technology, and not the maximum digitization frequency desired in principle for the purpose of this invention.

Figure 13:
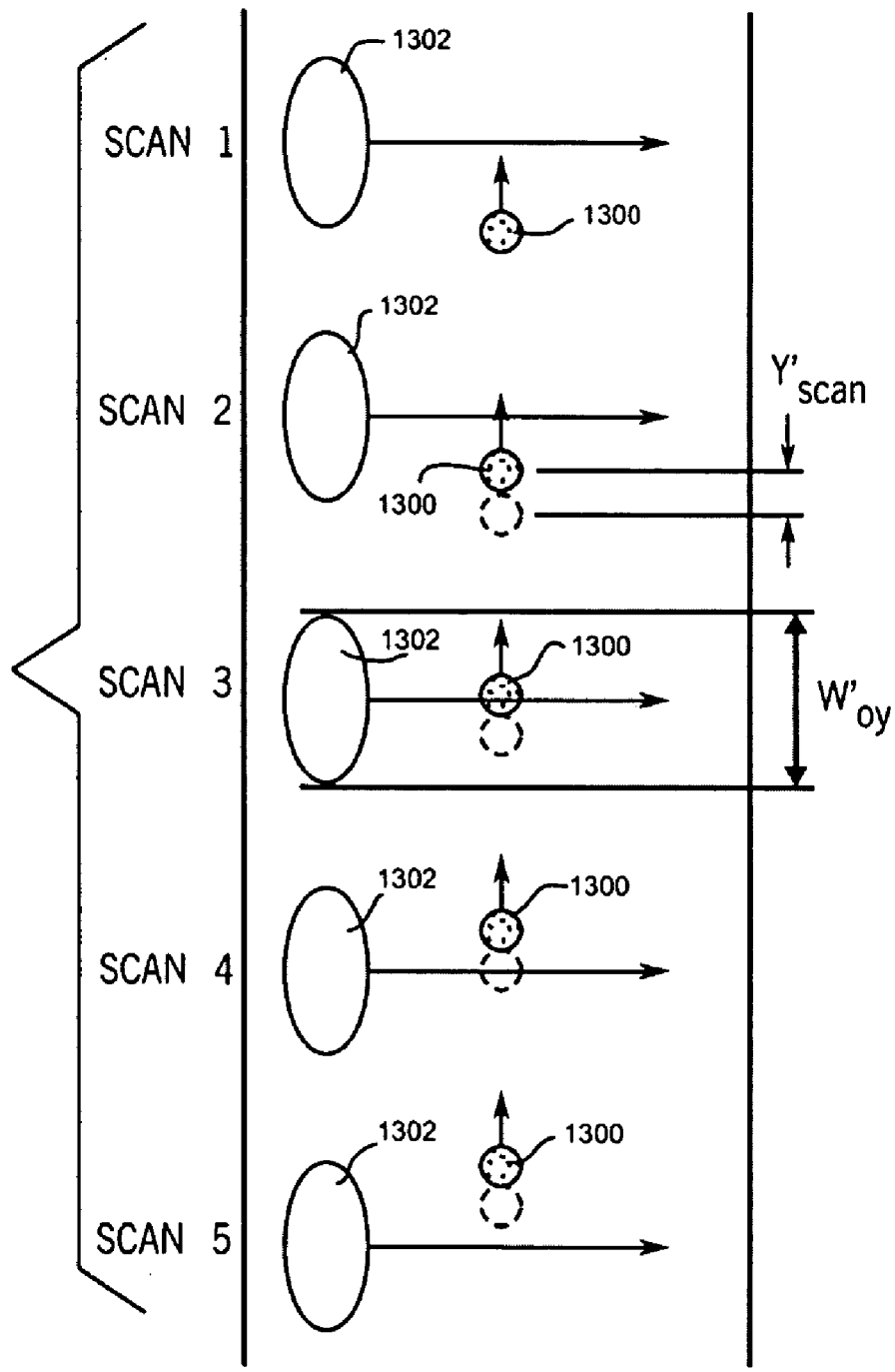
FIG. 13 is a schematic diagram illustrating the laser beam interacting repeatedly with a cell in the course of five consecutive raster scans.

Turning now to the multiple raster scans parameter, hypothetical scans 1, 2, 3, 4, and 5 of FIG. 13 diagrammatically show the position of a cell 1300 during each of a plurality of scans of the laser beam 1302. Here $y'_{scan}$ represents the distance advanced by a cell during one scan, and $w'_{oy}$ represents the beam spot size along the vertical axis of the elliptical beam. Based on the following relationships, i.e.:

$$t'_{raster} = \frac{1}{f'_{raster}} \qquad \text{raster period}$$

$$y'_{scan} = v'_{stream} t'_{raster}$$

$$= \frac{v'_{stream}}{f'_{raster}} \qquad \text{distance advanced in one scan}$$

$$w'_{oy} \qquad \text{vertical beam spot size}$$

condition #6 (multiple raster scans over cell) can be defined by the following relationship:

$$\frac{w'_{oy} f'_{raster}}{v'_{stream}} \geq 3 \qquad \text{condition \#6}$$

where the number 3 is selected to indicate the minimum number of scans required to allow, in principle, a reconstruction of the Gaussian curve representing the interaction between the laser beam and a cell in the course of multiple raster scans.

For condition #7 (rastering constraint), the mechanism of AODs is such that a trade-off relationship can exist between the range of deflection angles and the frequency of rastering. For the purpose of the current invention, the range of deflection angles can be relatively small, while the highest possible frequency of rastering is desired. Commercially available AODs optimized for this purpose can effect sweeps over approximately 1 to 2 mrad at a maximum repetition frequency of approximately 1 MHz. Therefore, $$f_{raster} \leq 1 \text{ MHz} \qquad \text{condition \#7}$$

where the condition is meant to indicate the constraint imposed by the performance of currently available technology, and not the maximum rastering frequency desired in principle for the purpose of this invention.

Figure 14:
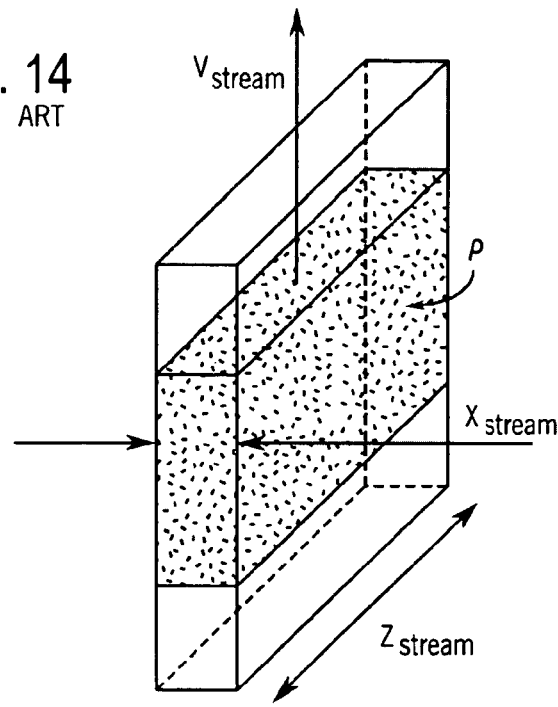
FIG. 14 is a schematic diagram of a volume of sample interrogated by a laser beam in a given unit of time in the prior art.
Figure 15:
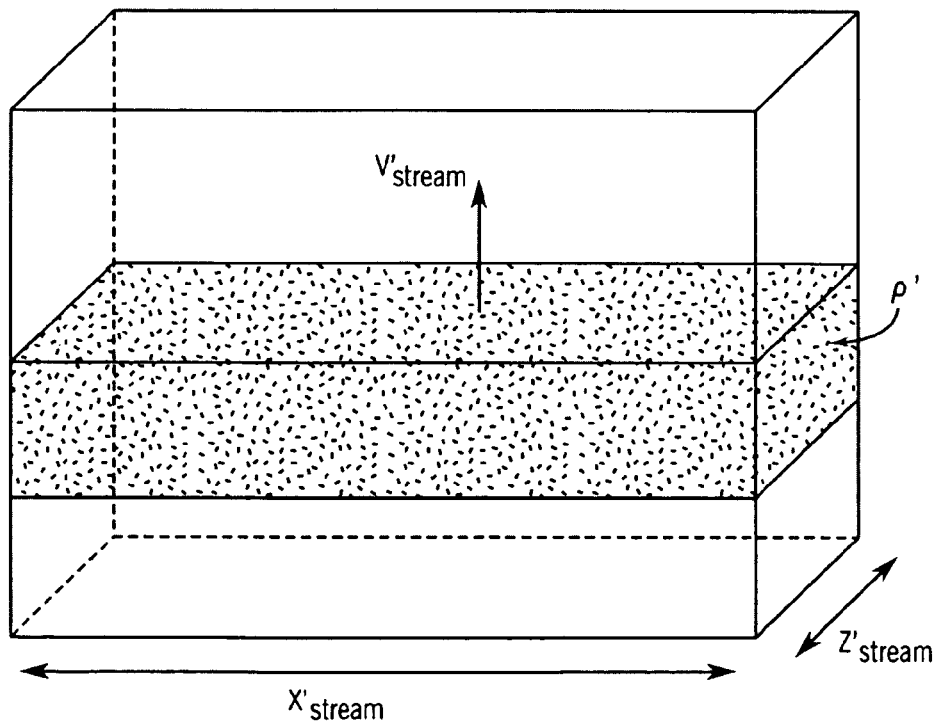
FIG. 15 is the analogue of FIG. 14 for the present invention.

Turning now to the measurement rate parameter, FIG. 14 shows diagrammatically a volume of sample of the prior art measured in a given unit of time and FIG. 15 shows diagrammatically a volume of sample measured in the same unit of time, according to the apparatus and method described herein, which volume can be substantially larger than that in the prior art. The reason for the difference is that in the prior art, the volume measured per unit time depends mainly on the illuminated volume and on the stream velocity, whereas in the apparatus and method described herein, the volume measured per unit time is augmented by the rastering process to include multiples of the illuminated volume. It is important to differentiate between the measurement volumes indicated in FIGS. 14 and 15 and the volume illuminated by the laser beam at any one instant of time, which is depicted in FIGS. 10 and 11 for the prior art and for the apparatus and method described herein, respectively, where such illuminated volume is intended to be substantially equivalent in the apparatus and method described herein and in the prior art, for an unchanged level of dilution. The following two relationships provide parameters to determine the measurement rate (defined as the number of cells detected per unit time), where the term "current" refers to the prior art and the term "new" refers to the present invention:

$n = \rho x_{stream} z_{stream} v_{stream}$ current measurement rate (cells/sec)

$n' = \rho' x' z'_{stream} z_{stream} v'_{stream}$ new measurement rate (cells/sec)

Condition #8 (measurement rate requirement) is defined by the following relationship:

$$\rho' x'_{stream} z'_{stream} v'_{stream} \geq \rho x_{stream} z_{stream} v_{stream} \quad \text{condition #8}$$

The foregoing relationships allow one to select choices for each parameter and verify that each condition is satisfied, and by what margin. The following set of approximate choices represents an embodiment suitable for use in this invention:

$P'_{laser} = 40$ mW
$w'_{ox} = 10$ μm
$w'_{oy} = 20$ μm
$x'_{stream} = 100$ μM
$z'_{stream} = 40$ μm
$v'_{stream} = 4$ m/s
$f'_{raster} = 1$ MHz
$f'_{digitization} = 100$ MHz where the choice of laser power is made by taking into consideration both condition #1 and condition #2. Of the two conditions, condition #2 is the more restrictive condition. The foregoing values are contrasted, for example, with the approximate values currently employed in the CELL-DYN®Sapphire® hematology analyzer:

$P_{laser} = 10$ mW
$w_{ox} = 65$ μm
$w_{oy} = 20$ μm
$x_{stream} = 5$ μm
$z_{stream} = 80$ μm
$v_{stream} = 8$ m/s Through appropriate choices of parameters, all of the conditions previously described can be satisfied, and some can be satisfied by a significant margin. Most importantly, the condition #8 yields the dramatic result of a five-fold improvement in measurement rate with respect to what is currently achieved on the CELL-DYN® Sapphire® instrument. It is understood that this level of improvement in measurement rate is indicative of a value that can be substantially increased, within the scope of the present invention, by judicious engineering choices or by improvement of performance of utilized components. It is also understood that the foregoing choices for parameter values for the present invention are tolerant of significant variation without an attendant significant reduction in the value of the invention. For example, the rastering frequency can be reduced by some amount or the sample stream dimensions can be altered in order to satisfy engineering design requirements, while still providing the present invention with a substantial advantage in terms of measurement rate, relative to the prior art.

Figure 16:
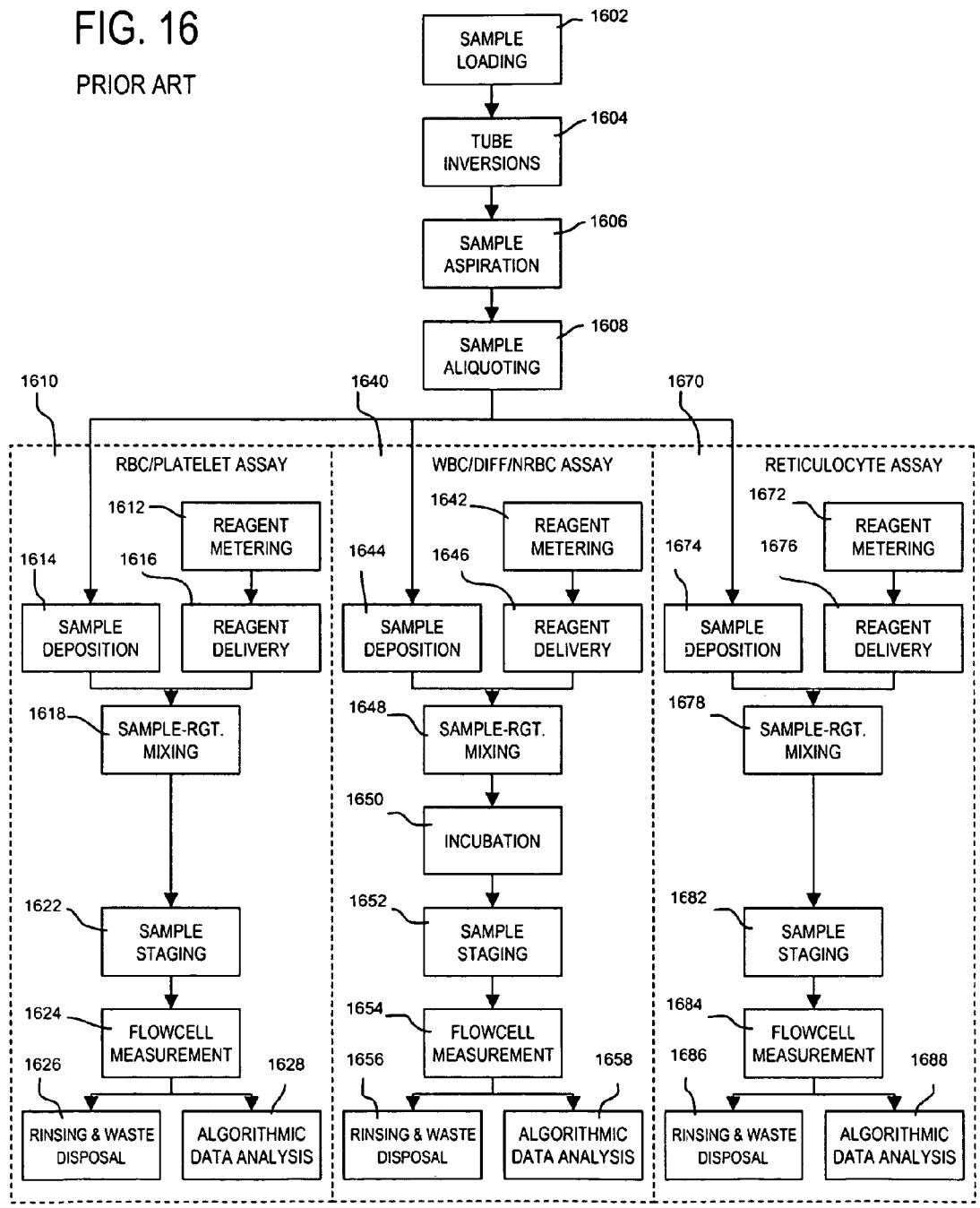
FIG. 16 is a schematic block diagram showing the essential functional steps of hematology analyzers of the prior art.

The overall sequence of main functional steps involved in the operation of a hematology analyzer of the prior art is depicted schematically in FIG. 16. A sample is loaded into the analyzer through a mechanical interface (1602). This interface typically takes the form of a sample loader system that can handle sets of racks of pluralities of sample tubes placed in a loading area attached to the analyzer, or, optionally, the form of an automation system that can handle either individual sample tubes or an individual rack containing a plurality of sample tubes, wherein either the individual sample tubes or the individual racks of sample tubes are conveyed on a track assembly. Once the sample tube advances to the requisite position, the sample tube is transferred to a mixing assembly that inverts the sample tube multiple times to ensure homogeneity of the sample (1604). Each tube containing a sample is then moved to a position to allow reading of an identifying barcode label or radio frequency identification tag (not shown), and the closure of the sample tube, typically a rubber stopper, is pierced by a probe assembly. The probe descends into the sample volume and aspirates a quantity of sample (1606). This aspirated volume is then partitioned into several aliquots by one of various means, such as, for example, passing through a shear valve with fixed volumes for the different aliquots, or dynamically pipetting the various aliquots directly into their next stages of processing (1608). The different aliquots then proceed through similar parallel paths corresponding to the respective assays to which they are allocated, such as, for example, the RBC and platetet assay (1610); the WBC, WBC differential, and an assay for optional flagging, identification, and quantification of nucleated RBCs (1640); and, optionally, the reticulocyte assay (1670). Other assays not shown, but substantially similar to those shown, include an assay for quantification of parameters related to hemoglobin, generally carried out on a separate calorimetric transducer requiring a strong lysing agent, and a separate aliquot of the sample; and an assay for counting and sizing certain subpopulations of blood cells, which is generally carried out on one or more separate impedance-based transducers. For each of these assays, the respective aliquot is transferred into an appropriate container (1614, 1644, and 1674). Separately, the respective reagent solution appropriate for the particular assay is metered precisely, typically by means of a motor-actuated syringe, a diaphragm pump, a peristaltic pump, or other suitable fluidic management component or subassembly (1612, 1642, and 1672). The precise amount of reagent solution is then delivered to the same container that receives the aliquot of the sample (1616, 1646, and 1676), or is otherwise brought into contact with the aliquot of the sample for the purpose of carrying out a reaction therewith. The mixture of aliquot of the sample and the reagent solution, in each separate assay, is homogenized, either by the process of introducing the sample and the reagent solution into the container, or by active mixing, such as, for example, by vortex mixing, through bubbles, agitation, turbulence, or other means (1618, 1648, and 1678). Depending on the assay, the homogenized mixture is then either transferred essentially immediately to a staging fluidic section (1622 and 1682), or is first incubated for a certain time, typically at a well-defined temperature, in the mixing container (1650), followed by transfer to a staging fluidic section (1652). This procedure is followed, for example, for WBC assays in the prior art, where RBCs are essentially removed by lysis during this incubation step. The various mixtures of the sample and the reagent solution, thus prepared, are then ready to enter the flowcell for measurement. In the case of hemoglobin measurements, the reacted aliquot of the sample can be measured colorimetrically in the same container in which the sample was mixed with and reacted with the lysing agent; in the case of impedance measurements, the aliquot of the reacted sample is directed to the impedance transducer rather than to the optical flowcell. A flow cytometer typically has a single flowcell, which then accepts the various prepared samples in some sequence and where the flow cytometry measurements take place serially (for example, 1624, 1654, and 1684). The samples are then processed for disposal, and the flowcell rinsed between adjacent measurements (1626, 1656, and 1686). As the samples are passed through the flowcell, the resulting signals undergo processing and are passed to the operating system of the analyzer for analysis by the cell counting, identification, and flagging algorithms (1628, 1658, and 1688).

The analogue of FIG. 16 for the apparatus and method described herein is depicted schematically in FIG. 17. In the description of the embodiment that follows, no separate hemoglobin transducer is present; for an embodiment including such a transducer in addition to the rastering optical flowcell, the incorporation of such a transducer adheres to schemes disclosed in the prior art and need not be shown here. The initial stages of the sample preparation are similar to those of the prior art, with the analogous steps of sample loading (1702), sample homogenization (1704), and sample aspiration (1706). The step of providing aliquots of the sample is eliminated, because a single volume of the sample is used for processing. The three or more separate assays of the prior art are combined into a single assay (1710), which yields those parameters that in the prior art require an assay for RBC and platelet parameters, an assay for WBC, WBC differential, and nucleated RBC parameters, an assay for quantification of reticulocyte parameters, and an assay for quantification of parameters related to hemoglobin. The volume of sample is delivered to a single container (1714), and the reagent solution is metered (1712) and delivered to the same container (1716). The resulting mixture is homogenized (1718); however, no incubation is necessary because of the absence of a lysing process. The mixture of the sample and the reagent solution is then staged (1722) and immediately passed through the flowcell, where the flow cytometer measurements take place (1724). There are no separate sample mixtures to be processed sequentially; therefore, the sample is directed to waste and the flowcell rinsed (1726), thereby allowing another sample to follow immediately. The signals from the flowcell measurements are processed and analyzed by the algorithms (1728).

Figure 18:
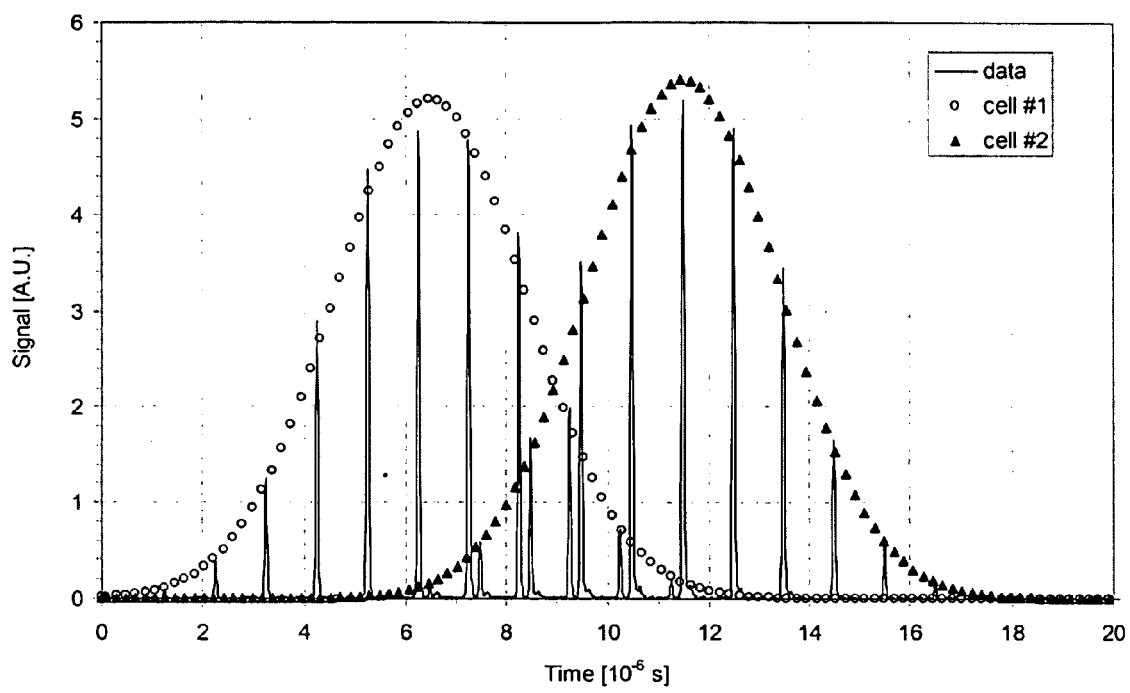
FIG. 18 is a graph showing actual data collected on an apparatus of the present invention, demonstrating the improved ability to resolve coincidences between nearby cells in the flow stream.

FIG. 18 is a portion of a collection of actual data from the method and the apparatus described herein. The data illustrate several key principles of lysis-free single-dilution method involving laser rastering: (a) the fast interaction between the laser beam and the cells, (b) the multiple periodic interactions of the beam with the same cell over several raster scans, (c) the rise-and-fall character of the multiple interactions, and (d) the ability of laser rastering to distinguish closely positioned cells in the sample stream (coincidences), which enables the high measurement rate required for single-dilution methods. The graph shows three plots: (1) the solid line represents actual data obtained from a rastering apparatus described herein acting on a diluted sample of human whole blood that was not subjected to a lysing agent, the apparatus operating at a raster scan frequency of 1 MHz and at a digitization frequency of 104 MS/s; (2) the open circles are a guide for the eye, and they represent the approximate Gaussian envelope of one series of peaks in the data; and (3) the closed triangles are another guide for the eye, and they represent the approximate Gaussian envelope of a second series of peaks in the data. Each series of peaks in the actual data is the result of the interaction of the rastering laser beam with one cell in the flow stream; the two series of peaks are interlaced, indicating an event, resolved by the analyzer described herein, which would have been unresolved (i.e., a coincidence) in an analyzer of the prior art. The captured data sequence is a demonstration of rastering operation that illustrates the schematic scenario of cells 801 and 803 depicted in FIGS. 8A through 8M. The two Gaussian envelopes show that the two peak series have similar widths, as would be expected from interaction sequences of like cells. The two cells in this case were RBCs.

The apparatus and method described herein can be used with any product line that employs a laser, or other suitable light source, for carrying out flow cytometry or flow-cytometer-based hematology analysis. Instruments that are suitable for use with this invention include, but are not limited to, the CELL-DYN® Sapphire® (commercially available from Abbott Laboratories) and the CELL-DYN® Ruby® (commercially available from Abbott Laboratories).

One benefit of the apparatus and method described herein is a dramatic increase in the measurement rate (cells analyzed per second), such as, for example, by an approximate factor of five. This increase allows (a) a reduction in the time for acquisition of data (time for counting cells) by the same factor, thereby increasing the throughput; or (b) an increase in the total counts (total number of cells counted) by the same factor, thereby increasing precision. An increase in precision is particularly important in cytopenic patients. A combination of increases in both precision and throughput is also feasible.

The specific effect that the combination of laser rastering and the lysis-free single-dilution method described herein would have on actual throughput (CBC/hr) can be estimated by making the following assumptions: (1) the RBC lysis incubation step of a conventional method is removed; (2) the multiple assays of a conventional method are combined into a single assay; (3) the measurement rate of a conventional analyzer is increased fivefold due to the adoption of laser rastering; (4) the total count time of the combined assay is based on this increased measurement rate, on the highest cell concentration given the allowable coincidence rates (i.e., that concentration given by the dilution ratio of a conventional RBC/platetet assay), and on matching the desired WBC precision levels to those achieved in a WBC assay of the conventional method.

A method based on these assumptions would result in a reduction of the measurement time for a CBC to about 15 seconds. Allowing for some margin for rinsing the flowcell to reduce carryover, a typical "ready-to-ready" processing cycle time can be estimated to be approximately 16 seconds, corresponding to an estimated average throughput of 225 CBC/hr. This is contrasted with the current performance of the CELL-DYN® Sapphire® (105 CBC/hr), which combines the relatively high throughput of the prior art with high first-pass reportability; and with the best in-class throughput of 150 CBC/hr, albeit at a relatively lower rate of first-pass reportability. This level of effective throughput improvement, coupled with best-in-class first-pass reportability, would be extremely significant from a commercial perspective.

An attendant benefit of the apparatus and method described herein in a hematology analyzer or flow cytometer is the ability to independently determine multiple parameters closely correlated with the size of the particle(s) being subjected to measurement. Determining the size of cells in the sample is one of the principal functions of a hematology analyzer. In the prior art of instrumentation based on flow cytometers, determination of cell size is typically achieved by processing the signal from one or more of the scattering detectors, particularly the forward-scattering detectors, or by one or more additional dedicated transducers operating on the principle of cell sizing based on impedance measurements. This scattering capability of the prior art is available, unchanged, in the apparatus and method described herein. Another approach taken in the prior art has been to measure the so-called "time of flight," namely the time it takes a particle to traverse the stationary laser light beam spot. Referring to FIG. 5, i.e., the prior art, time of flight would be approximately represented by the width of the interaction signal curve 506. (This is actually a correlation of the size of the particle and the width of the laser beam spot; if the laser beam spot size is known, the particle size can be determined.) In the apparatus and method described herein, there are several opportunities for obtaining a time-of-flight measurement of the size of the cell under scrutiny. First, each raster scan that interacts with a cell can optionally return a value for the width of such interaction. Referring to FIGS. 7A, 7B, and 7C, the width of each of the interaction curves represents an independent measurement of the size of the cell 702. The availability of a multiplicity of such determinations provides a statistical robustness of precision to the collection of size values that is unmatched by a single determination, such as is used in the prior art. Second, referring to FIG. 7D, the correlation across raster scans that yields the peak value 710 of the interaction curve 712 can likewise yield the width of such interaction. This determination represents an additional measurement of the size of the cell, which can be combined and correlated with the determinations from each raster scan to result in a robust collection of measurements related to size not only independent of, but also augmenting, those derived from the scattering information itself.

A significant benefit derived from the apparatus and method described herein is the reduction in components, subsystems, reagents, operating firmware, operating software, and overall design complexity that is enabled by the lysis-free single-dilution approach being combined with the rastering method. For example, each of the two or more delivery subsystems that is eliminated by adoption of the present invention would typically include the following components: (a) a precision metering syringe; (b) a syringe assembly; (c) a syringe stepper motor; (d) a stepper motor driver board; (e) several lengths of noncompliant tubing; (f) several pinch valves; (g) the corresponding pilot valves that operate the pinch valves, or alternatively the solenoids operating the pinch valves; (h) the electronic board components driving the pilot valves or the solenoids; (i) a container used to mix one aliquot of sample with the metered quantity of reagent; (j) a motor used to mix the sample aliquot with the reagent solution; (k) the mixer motor driver board; (l) the firmware necessary to control operation of the stepper motor, the mixer motor, and the several pilot valves or solenoids; (m) the current capacity necessary to power the stepper motor, the mixer motor, and the pilot valves or solenoids; (n) the fans necessary to remove the heat from the flow panel due to operation of the pilot valves or solenoids. Taking as example the CELL-DYN®Sapphire®, where three reagent delivery subsystems supporting flow cytometry measurements are currently in use (that for the RBC/platetet assay; that for the WBC, WBC differential, and nucleated RBC assay; and that for the optional reticulocyte assay), adoption of the apparatus and method described herein would reduce these to a single reagent delivery subsystem. Subsystems supporting impedance measurements (for cell volume determination) or calorimetric measurements (for hemoglobin determination) need not be affected. However, these subsystems, too, could optionally be eliminated altogether for additional benefits in simplicity, reliability, and cost, because the apparatus and method used for lysis-free single-dilution approach could provide all of the reportable parameters (including mean cell volume and average hemoglobin content) that are required of a commercial hematology analyzer.

The apparatus and method described herein can be utilized in various environments through the use of a modular approach. A very fast version (leveraging the aspect of the apparatus and method related to the reduction in the time required for a CBC) can be used for high-volume applications in reference laboratories and hospital core laboratories, optimized for effective throughput, and possibly without monoclonal antibody features. A very precise version (leveraging the aspect of the apparatus and method related to the increase in total number of counted cells in a given unit of time) can be aimed at tertiary-care centers, optimized for performance on rare events and cytopenic samples, and including monoclonal antibody features.

The reagents used in the analyzer are reduced from the set in the prior art (which includes a lysing agent for use in the WBC assay, an optional nucleic acid dye added to the lysing agent for use in the concurrent nucleated RBC assay, a diluent solution containing optional sphering reagent for the RBC/platetet assay, and a reagent solution used for the reticulocyte assay, which reagent solution includes a nucleic acid dye, and, optionally, a strong lysing agent used for hemoglobin quantification) to a single reagent solution, which comprises a diluent, typically a saline diluent. The single reagent solution preferably comprises a sphering reagent. The single reagent solution optionally comprises one or two nucleic acid dyes for reticulocyte and NRBC analysis. At least one of the nucleic acid dyes should be capable of staining RNA, and at least one of the nucleic acid dyes should be capable of staining DNA. Alternatively, the at least one nucleic acid can be capable of staining both RNA and DNA. Another optional ingredient of the reagent solution for use in the method described herein is a selective permeabilizing agent. Only one dilution ratio is used. The cell counting and identification algorithms are combined from a set dedicated to each of the currently employed assays to a single set to be applied to the single assay being performed. Furthermore, the algorithms employ the same data (signals) that are currently employed. The precision of results can be automatically maintained by design. The coincidence levels can be maintained by design. Problems caused by misalignment of laser beam and sample stream on account of temperature fluctuations can be eliminated. The beam "self-registers" to the sample stream with each rastering cycle, rendering slow drifts inconsequential. The entire extent of the laser beam is used, as opposed to just the small central portion of it, resulting in greater efficiency for a given power level. In the prior art, 90-95% of the beam is wasted. Finally, the stream velocity is reduced, thereby causing the system to move away from the turbulence threshold, with reduced risk for hydrodynamic instabilities.

Various modifications and alterations of this invention will become apparent to those skilled in the art without departing from the scope and spirit of this invention, and it should be understood that this invention is not to be unduly limited to the illustrative embodiments set forth herein.

What is claimed is:
1. A lysis-free single dilution method for operating a hematology analyzer, the method comprising:
(a) providing a laser rastering apparatus having
(i) a source of light,
(ii) a flowcell containing a moving sample stream, whereby particles in the sample move with the sample stream,
(iii) at least one optical element for focusing light from the source of light onto the particulate material moving with the sample stream in the flowcell,
(iv) a scanning device for deflecting the focused light from the source of light to enable the focused light to sweep back-and-forth across the moving sample stream,

(v) a cylindrical lens to compensate for optical distortions introduced into the light beam by the action of the scanning device,
(vi) at least one detector channel, and
(vii) circuitry for processing signals;
(b) providing a sample of body fluid;
(c) homogenizing the sample of body fluid;
(d) extracting a volume of the sample of body fluid;
(e) introducing a reagent solution, free of a lysing agent, to the volume extracted to form a mixture;
(f) homogenizing the mixture of step (e); and
(g) analyzing the resulting homogenized mixture by means of the apparatus.

2. The method of claim 1, wherein said flowcell has cross-sectional dimensions sufficient to enable the formation of a sample stream in which a plurality of particles can flow along side of one another.

3. The method of claim 1, wherein said scanning device is a dynamic beam deflector.

4. The method of claim 1, wherein the apparatus further includes a conditioning circuit for an analog signal.

5. The method of claim 1, wherein said at least one detector channel comprises at least one member selected from the group consisting of a preamplifier circuit, an analog-to-digital converter, and a field-programmable gate array.

6. The method of claim 4, further including a digital signal processing chip, sufficient on-board memory registers to hold intermediate values for computation, and a digital-to-analog converter.

7. The method of claim 1, wherein said determination of parameters is carried out by means of time-of-flight measurements.

8. The method of claim 1, wherein said scanning device is an acousto-optic modulator.

9. The method of claim 1, wherein the body fluid is blood.

10. The method of claim 1, wherein the body fluid is selected from the group consisting of cerebrospinal fluid, pleural fluid, peritoneal fluid, pericardial fluid, synovial fluid, ascites fluid, drainage fluid, and dialysate fluid.

11. The method of claim 1, wherein the sample of body fluid is homogenized by inversion.

12. The method of claim 1, wherein the volume is extracted by aspiration.

13. The method of claim 1, wherein aspiration is carried out by dynamic pipetting.

14. The method of claim 1, wherein aspiration is carried out by shear valve.

15. The method of claim 1, wherein homogenization of the mixture of step (e) is carried out by vortex mixing.

16. The method of claim 1, wherein homogenization of the mixture of step (e) is carried out by bubble mixing.

17. The method of claim 1, wherein homogenization of the mixture of step (e) is carried out by turbulent mixing.

18. The method of claim 1, wherein the reagent solution comprises a saline diluent.

19. The method of claim 18, wherein the reagent solution further includes a sphering reagent.

20. The method of claim 19, wherein the reagent solution further includes at least one nucleic acid dye.

21. The method of claim 20, wherein the at least one nucleic acid dye is capable of staining RNA.

22. The method of claim 20, wherein the at least one nucleic acid dye is capable of staining DNA.

23. The method of claim 18, wherein the reagent solution further includes a selective permeabilizing agent.

24. A lysis-free single dilution method for operating a hematology analyzer, the method comprising:
(a) providing a laser rastering apparatus having
   (i) a source of light,
   (ii) a flowcell,
   (iii) at least one optical element for focusing light from the source of light onto a sample stream within the flowcell,
   (iv) a scanning device for deflecting the focused light from the source of light to enable the focused light to sweep back-and-forth across the sample stream,
   (v) at least one detector channel, and
   (vi) circuitry for processing signals received from the detector channel;
(b) homogenizing a sample of body fluid;
(c) introducing a reagent solution, free of a lysing agent, to the sample of body fluid to form a mixture;
(d) homogenizing the mixture of step (c); and
(e) analyzing the resulting homogenized mixture by means of the apparatus.

* * * * *